United States Patent
Inzé et al.

(10) Patent No.: US 10,801,032 B2
(45) Date of Patent: Oct. 13, 2020

(54) MEANS AND METHODS FOR YIELD PERFORMANCE IN PLANTS

(71) Applicants: VIB VZW, Ghent (BE); Universiteit Gent, Ghent (BE)

(72) Inventors: Dirk Gustaaf Inzé, Moorsel-Aalst (BE); Hannes Claeys, Cold Spring Harbor, NY (US); Hilde Nelissen, Ghent (BE); Xiaohuan Sun, Ghent (BE)

(73) Assignees: VIB VZW, Ghent (BE); Universiteit Gent, Ghent (BE)

( * ) Notice: Subject to any disclaimer, the term of this patent is extended or adjusted under 35 U.S.C. 154(b) by 267 days.

(21) Appl. No.: 14/895,918

(22) PCT Filed: Jun. 3, 2014

(86) PCT No.: PCT/EP2014/061438
§ 371 (c)(1),
(2) Date: Dec. 3, 2015

(87) PCT Pub. No.: WO2014/195287
PCT Pub. Date: Dec. 11, 2014

(65) Prior Publication Data
US 2016/0130602 A1 May 12, 2016

(30) Foreign Application Priority Data
Jun. 3, 2013 (GB) .................... 1309866.0

(51) Int. Cl.
*C12N 15/82* (2006.01)

(52) U.S. Cl.
CPC ..... *C12N 15/8229* (2013.01); *C12N 15/8261* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 2003/0199681 A1* | 10/2003 | Fincher | C12N 9/1092 536/23.2 |
| 2007/0039067 A1* | 2/2007 | Feldmann | C07K 14/415 800/278 |
| 2007/0130645 A1 | 6/2007 | Wu et al. | |
| 2009/0178163 A1 | 7/2009 | Wu et al. | |
| 2011/0078833 A1 | 3/2011 | Wu et al. | |
| 2012/0240287 A1 | 9/2012 | Fu et al. | |

FOREIGN PATENT DOCUMENTS

| | | | |
|---|---|---|---|
| EP | 1198985 | | 4/2002 |
| WO | WO2006/138012 | * | 12/2006 |
| WO | 2011067712 | | 6/2011 |
| WO | WO2011/008065 | * | 7/2011 |
| WO | WO2011/088065 | * | 7/2011 |
| WO | WO2013/108017 | * | 7/2013 |
| WO | WO2013/108017 A1 | * | 7/2013 |
| WO | 2014195287 | | 12/2014 |

OTHER PUBLICATIONS

Oh et al., Plant Cell 19:1192-208 (2007).*
Bak et al., "Cytochromes P450" in The *Arabidopsis* Book, pp. 1-56 (2011).*
Wang et al., Plant Cell 20:1231-43 (2008).*
Nelson, Meth Mol Biol 320:1-10 (2004).*
Schomburg et al., Plant Cell 15:151-63 (2003).*
Zondlo & Irish, Plant J 19(3):259-68 (1999).*
Anastasiou et al., Develop Cell 13:843-56 (2007).*
Crane, Phil Trans Biol Sci 359:735-37 (2004).*
Li et al., Plant Sci 285:1-13 (2019).*
Potenza et al., In Vitro Cell Dev Biol Plant 40:1-22 (2004).*
Bak et al., "Cytochromes P450" in The *Arabidopsis* Book, pp. 1-56 (2011), pp. 1-2.*
Zhang, Curr Opin Plant Biol 6:430-40 (2003).*
Whisstock & Lesk, Q Rev Biophys. 36(3):307-40 (2003).*
Sugaya & Uchimiya (1992) Plant Physiol 99:464-67.*
Baumlein et al. (1992) Plant J 2(2):233-39.*
Sun et al. (2017) Nat Comm 8:14752.*
PCT International Search Report dated Aug. 13, 2014, PCT/EP2014/061438.
Elena Anastasiou et al., Control of Plant Organ Size by KLUH/CYP78A5-Dependent Intercellular Signaling, Develpmental Cell, Dec. 4, 2007, pp. 843-856, vol. 13, No. 6.
Krizek et al., Making bigger plants: key regulators of final organ size, Current Opinion in Plant Biology, Feb. 1, 2009, pp. 17-22, vol. 12, No. 1, Quadrant Subscription Services.
Jia-Wei Wang et al., Dual Effects of miR156-Targeted SPL Genes and CYP78A5/KLUH on Plastochron Length and Organ Size in *Arabidopsis thaliana*, The Plant Cell, May 2008, pp. 1231-1243, vol. 20, American Society of Plant Biologists.
Tomoaki Sakamoto et al., Expression of Gibberellin 2-Oxidase Gene around the Shoot Apex is Related to Phase Transition in Rice, Plant Physiology, Mar. 1, 2001, pp. 1508-1516, vol. 125, American Society of Plant Physiologists.
Stephen G Thomas et al., Molecular cloning and functional expression of gibberellin 2-oxidases, multifunctional enzymes involved in gibberellin deactivation, Proceedings of the National Academy of Sciences, Apr. 1, 1999, pp. 4698-4703, vol. 96, National Academy of Sciences.
David R Nelson, Cytochrome P450 nomenclature, 2004, Methods in Molecular Biology, Jan. 1, 2006, pp. 1-10, vol. 320, Humana Press Inc.

(Continued)

*Primary Examiner* — Russell T Boggs
(74) *Attorney, Agent, or Firm* — Patent Law Works, LLP

(57) ABSTRACT

This disclosure relates to the field of plant molecular biology; more particularly to the field of agriculture; even more particularly to the field of improving the yield of plants. This disclosure provides chimeric genes and constructs that can be used to enhance the yield in plants and crops.

5 Claims, 10 Drawing Sheets
Specification includes a Sequence Listing.

(56) References Cited

OTHER PUBLICATIONS

Felsenstein, J., Confidence Limits on Phylogenies: An Approach Using the Bootstrap, Evolution, Jul. 1985, pp. 783-791, vol. 39, No. 4.

Nelissen et al., "A Local Maximum in Gibberellin Levels Regulates Maize Leaf Growth by Spatial Control of Cell Division", Current Biology, 2012, pp. 1183-1187, vol. 22, XP028404183, DOI: doi:10.1016/j.cub.2012.04.065.

Nelissen et al., "Plant Organogenesis", 2013, Humana Press, article "Kinematic Analysis of Cell Division in Leaves of Mono- and *dicotyledonous* Species: A Basis for Understanding Growth and Developing Refined Molecular Sampling Strategies", pp. 247-264.

Saitou et al., The neighbor-joining method: A new method for reconstructing phylogenetic trees, Molecular Biology and Evolution, 1987, pp. 406-425, vol. 4.

Sun et al., Altered expression of maize Plastochron1 enhances biomass and seed yield by extending cell division duration, Nature Communication, published Mar. 16, 2017, pp. 1-11, DOI: 10.1038/ncomms14752|www.nature.com/naturecommunications.

Tamura et al., MEGA5: Molecular Evolutionary Genetics Analysis Using Maximum Likelihood, Evolutionary Distance, and Maximum Parsimony Methods, Mol. Biol. Evol., May 4, 2011, pp. 2731-2739, vol. 28, No. 10, DOI: 10.1093/molbev/msr121.

Zuckerkandl et al., Evolutionary divergence and convergence in proteins, Edited in Evolving Genes and Proteins by V. Bryson and H.J. Vogel, 1965, pp. 97-166, Academic Press, New York.

Gou et al., Tissue-specific Expression of Populus C19 GA 2-Oxidases Differentially Regulate Above- and Below-Ground Biomass Growth Through Control of Bioactive GA Concentrations. New Phytologist, (2011) 192, pp. 626-639.

Sakamoto et al., Expression of a Gibberellin 2-Oxidase Gene Around the Shoot Apex Is Related to Phase Transition in Rice., Plant Physiology (2001) vol. 125, pp. 1508-1516.

\* cited by examiner

GGGGACAACTTTGTATAGAAAAGTTGCCGAGGATTGCAGCTCCTGGATCATATCAGAATGTCT
GTCGCTCGCCACCCCGGGCGCACTGCATTATATTTCTGGCAGGTGCGCAATACAATATGGCA
TGGGGGGCACGTAGTACGGTACTGCCGTACAGCTGCGTCAGCAAATGCCAACTTGTGTGGTA
CAGCTATAATCTATAGAAAAAGAATATTATAGAAGTAGTAGAAGTTGGCGCGTATGGATTAA
GGAAGGTTTGGTTTCTAGTGACTAATTTAGTCTCTCTATTTTATTCAATTTTGTTCCTAAATTATC
AAACTAAAATGAAGTTTTGTTTTTTTATATAGGATAATTTAGAGACTAAAATAGAATAAAAT
GAATGGATGAAAAATTAGTTCCTACCAACCAAACACCCCTTAAGAGCTACTTCGAGAACCTCA
AATCTCCTTCGAGACTGGAGGAGATGAAGGTAAAAATAAACTAATTTTCCCTTCAATCCTTTTA
ATTCACAAGGGGGTGCGGGTACGGAAATGTTTACTACTATACTGGAAAGGTGTCTGAAACCG
GGAGAAAAGCTTTGACCAGGGTGGACCTGTTTATGGGATCGAAGCGGCCGTTGCCCCAACTG
GCGACTGGCGAGCCACCATTGCGCGGACCCGAGATTAACTATACTACAGGAGTACTGTCGGG
TTGGTACCAATACGTGGCTTGGGCAAAAGTCTGGCAGGCGCCGCTGCTTGTCTGCGGTTTCT
ATGTGCCGATGCCATCGCACCGGACCGGATCGGATGGGATCAGCGGAACATGCGAGAGCG
AGCCTGCACTGCACTGCATGGCCGCGACCGCGTCGTCCATCGAGCCGCCTATCATTAGTTGG
TTCCACTGTCTCGCCGCCGAAGCAAGGCAGCACAGCACACATCAGCATTGCTTCCCAGTTCC
CAATGCCCCGTCGTCCTAGCCGAGGCGGGCTCAGTACCAACCCAGCTGAAACTACGAGAGAT
GCGCTGTGGGCAGGACAGTGGTCGAGCGAGGAGTGTACCTGTAGTTAACGAGGATTTTATTT
TACTAGTGCGTACGTACGTACTGTACGTACTATGATCTCTCACGTGCTCTGGTCTTATCACTCG
CTTGATTATACTATGATCTTTTTTTCCCTCCACCTGCTCTGGTCTTATCGCTGGCACGTGCTTTT
ACACGGCCACTTAGGACTACTCACCTCGTCTCGTCATGCTTATCTACTTCAGAGCGTCACGGA
CACAGCAAGGAGGAGTACGCACACGCAGCATGGACTGCCTGGAGCGGGGTGTGGTGCACTA
ACGCCCGCCTAATTCCCGGAGCTGCCTGTGCCTTGGACGCCATCTCTGGTTTCGCGGGGAG
AATAATAATAATTTAGGCGAAACACGGGAACGGGTCGTGAGGAAAAGCCTGACATGCTGCAT
TACGGCCGGTGCCGTTCGGACCCCAGTTATTGATGAGCCGAGTCACCGACCTGCCAAGAAAA
GGATGCCGGATCAAGGGCAGGTTCACCTCATCTTAGCGCATGCAAGCGTCGTCCCTAACCAA
AACATCATCTTCATGTCTGGCCGCCGCGCAGCGGTCCCAGTGCCGGCGTGGTTAACGGGAG
GGACTGGGACTGGCAGGGCCGGCTAATGGCCGACGTGCAGTCGCCTCGTATGCGTTTCCCGT
TGAGCCATGCATGCAGCAGAGCAGCGCGGGCGGCCGGTCCTGCCACCGGTGGATCGCGGCC
GGGCACGTCACGGCCCGGTCCCGACTGCTCTGGCTCCATCGCCGCCACCATGCACCCAAA
GCGATCCACCCCCGATGCATCCCTTTTCTCTCCCTGTCAGCTGGGCCCATCTCGCGTCACCGT
AGCCAGGTGCCGCCCCGTCGCCCCGCCCCCGATCTATATATGCTGCCCACGGGCTCTCCCA
CTTCTCCCCCACATGCACTTGCTGCAGCAGCCGTAGGACACACGCACACCGCCTCGACCTCG
AGTCCACCACTGACTCCACCACCTCCCCCTGTTTTTTTCGACCTCGCTCTGCTCATCCGCACG
GCCAGACAGCCGCAAGTTTGTACAAAAAAGCAGTCCCC

FIG. 1

GGGGACAAGTTTGTACAAAAAAGCAGGCTCCATGGCGATGGCCTCCGCGGCTTGCTCATG
CACGGACGGCACGTGGTGGGTGTACGCGCTCCCGGCGCTGCTCGGCTCCGACACCCTGTGC
GCCCACCCGGCCCTCCTGGCTGGCCTGATCTTTCTGGCCACCGTCTCGGTGGCTCTGCTGGC
GTGGGCCACGTCGCCGGGCGGTCCGGCGTGGACGAACGGCCGCGGCCGCCTCGGCGTCAC
TCCTATCGTGGGACCCCGTGGTCTGCCCGTGTTCGGCAGCATCTTCGCGCTGTCCCGCGGGC
TGCCGCACCGCGCCCTCGCCGAGATGGCCCGCGCCGCAGGGCCCCGGGCCAAGGAGCTCAT
GGCGTTCTCCGTCGGTGACACGCCCGCGGTCGTGTCGTCCTGCCCGGCCACGGCACGTGAG
GTGCTCGCGCACCCGTCATTCGCCGACCGCCCTGTGAAGCGGTCGGCCCGGGAGCTCATGTT
CGCGCGTGCCATCGGGTTCGCGCCCAACGGCGAGTACTGGCGCCGCCTCCGCCGCGTCGCG
TCCACGCACCTATTCTCCCCGCGCCGGGTCGCCTCGCACGAGCCGGGACGCCAAGGTGACG
CGGAGGCCATGCTCCGCTCCATCGCCGCCGAACAGTCGGCCTCTGGCGCCGTCGCCCTCCG
CCCGCACCTCCAGGCCGCCGCTCTCAACAACATCATGGGCAGCGTCTTCGGCACGCGGTACG
ACGTCACATCAGGCGCCGGCGCCGCGGAGGCCGAGCATCTCAAGAGCATGGTGCGCGAGG
GGTTCGAGCTCCTCGGCGCCTTCAACTGGTCCGACCACCTCCCCTGGCTCGCCCACCTGTAC
GACCCAAGCAACGTCACCCGCCGGTGCGCCGCGCTCGTGCCGCGCGTCCAGACCTTCGTCC
GTGGCGTCATCGACGAGCACCGGCGCCGCCGCCAAAACTCCGCCGCCCTCAACGACAATGC
TGACTTCGTCGACGTGCTCCTCTCCCTCGAGGGTGACGAGAAGCTCGGCGACGACGACATGG
TCGCCATCCTCTGGGTAAAGTTCAAATCGATCGCTTTCCTAGCTTGTTTAACTGCGCATACTTC
TCAGTTCTCAACTGCGCATACCTGTCGGTTCTACAGTTTTGTGTCGGGCTGTCGGTTGTTCCCG
GAAGGGAAAAAAAGAACAAAGCTCTGTCGCTGAAAAAAACATACTGTACATGCATATAATTT
GTTTTTGCAGGAGATGGTCTTCCGCGGTACGGACACGACGGCGCTTCTGACCGAGTGGTGCA
TGGCGGAGCTGGTGCGCCACCCGGCGGTGCAGGCGAGGGTGCGCGCCGAGGTCGACGCGG
CTGTCGGTGCCGGAGGTTGCCCCACCGACGCCGACGTGGCGCGCATGCCGTACCTGCAGGC
GGTTGTGAAGGAGACGCTGCGCGCCACCCGCCTGGCCCGCTGCTGAGCTGGGCTCGCCTC
GCCACCGCCGACGTGCCACTCTGCAACGGCATGGTGGTCCCGGCTGGCACCACGGCGATGG
TGAATATGTGGGCCATAACCCACGATGCCGCCGTGTGGGCCGACCCGGACGCGTTCGCGCC
GGAGCGGTTCCTGCCCTCCGAGGGCGGCGCCGACGTGGACGTCCGCGGCGTCGACCTCCGC
CTGGCCCCGTTCGGCGCCGGGCGTCGCGTCTGCCCCGGCAAGAACCTGGGCCTCACCACCG
TGGGCCTCTGGTTGCCCGCCTCGTGCACGCCTTCCAGTGGGCCCTGCCTGACGGCGCGGC
GGCCGTTTGCCTCGACGAGGTCCTCAAGCTCTCCCTGGAGATGAAGACGCCGCTCGTCGCCG
CAGCCATCCCCCGCACCGCCTGAGACCCAGCTTTCTTGTACAAAGTGGTCCCC

FIG. 2 caactttgtatagaaaagttgccgaggattgcagctcctggatcatatcagaatgtctgtcgctcgccaccccgggcgcactgcattatatttctg
gcaggtgcgcaatacaatatggcatggggggcacgtagtacggtactgccgtacagctgcgtcagcaaatgccaacttgtgtggtacagcta
taatctatagaaaaagaatattatagaagtagtagaagttggcgcgtatggattaaggaaggtttggtttctagtgactaatttagtctctctatttt
attcaattttgttcctaaattatcaaactaaaatgaagttttgttttttttatataggataatttagagactaaaatagaataaaaatgaatggatgaa
aaattagttcctaccaaccaaacacccccttaagagctacttcgagaacctcaaatctccttcgagactggaggagatgaaggtaaaaataaa
ctaattttcccttcaatccttttaattcacaaggggggtgcgggtacggaaatgtttactactatactggaaaggtgtctgaaaccgggagaaaag
ctttgaccagggtggacctgtttatgggatcgaagcggccgttgccccaactggcgactggcgagccaccattgcgcggacccgagattaac
tatactacaggagtactgtcgggttggtaccaatacgtggcttgggcaaaaagtctggcaggcgccgctgcttgtctgcggtttctatgtgccgat
gccatcgcaccggaccggatcgggatgggatcagcggaacatgcgagagcgagcctgcactgcactgcatggccgcgaccgcgtcgtc
catcgagccgcctatcattagttggttccactgtctcgccgccgaagcaaggcagcacagcacacatcagcattgcttcccagttcccaatgc
cccgtcgtcctagccgaggcgggctcagtaccaacccagctgaaactacgagagatgcgctgtgggcaggacagtggtcgagcgagga
gtgtacctgtagttaacgaggattttatttactagtgcgtacgtacgtactgtacgtactatgatctctcacgtgctctggtcttatcactcgcttgatta
tactatgatctttttttccctccacctgctctggtcttatcgctggcacgtgcttttacacggccacttaggactactcacctcgtctcgtcatgcttatct
acttcagagcgtcacggacacagcaaggaggagtacgcacacgcagcatggactgcctggagcggggtgtggtgcactaacgcccgcct
aattcccggagctgcctgtgccttggacgcccatctctggtttcgcggggagaataataataatttaggcgaaacacgggaacgggtcgtgag
gaaaagcctgacatgctgcattacggccggtgccgttcggaccccagttattgatgagccgagtcaccgacctgccaagaaaaggatgccg
gatcaagggcaggttcacctcatcttagcgcatgcaagcgtcgtccctaaccaaaacatcatcttcatgtctggccgcccgcgcagcggtccc
agtgccggcgtggttaacgggagggactgggactggcagggccggctaatggccgacgtgcagtcgcctcgtatgcgtttcccgttgagcc
atgcatgcagcagagcagcgcgggcggccggtcctgccaccggtggatcgcggccgggcacgtcacggcccggtccccgactgctctgg
ctccatcgccgccaccatgcacccaaagcgatccaccccgatgcatcccttttctctccctgtcagctgggcccatctcgcgtcaccgtagcc
aggtgccgccccgtcgccccgccccccgatctatatatgctgcccacgggctctcccacttctcccccacatgcacttgctgcagcagccgta
ggacacacgcacaccgcctcgacctcgagtccaccactgactccaccacctcccccctgtttttttcgacctcgctctgctcatccgcacggcc
agacagccgcaagtttgtacaaaaaagcaggctccatgcgatggcctccgcggcttgctcatgcacggacggcacgtggtgggtgtacg
cgctcccggcgctgctcggctccgacaccctgtgcgcccaccggccctcctggctggcctgatctttctggccaccgtctcggtggctctgctg
gcgtgggccacgtcgccgggcggtccggcgtggacgaacggccgcggccgcctcggcgtcactcctatcgtgggaccccgtggtctgccc
gtgttcggcagcatcttcgcgctgtcccgcgggctgccgcaccgcgccctcgccgagatggcccgcccgcagggccccgggccaagga
gctcatggcgttctccgtcggtgacacgcccgcggtcgtgtcgtcctgcccggccacggcacgtgaggtgctcgcgcacccgtcattcgccga
ccgccctgtgaagcggtcggcccgggagctcatgttcgcgcgtgccatcgggttcgcgcccaacggcgagtactggcgccgcctccgccgc
gtcgcgtccacgcacctattctccccgcgccgggtcgcctcgcacgagccgggacgccaaggtgacgcggaggccatgctccgctccatc
gccgccgaacagtcggcctctggcgccgtcgccctccgcccgcacctccaggccgccgctctcaacaacatcatgggcagcgtcttcggca
cgcggtacgacgtcacatcaggcgccggcgccgcggaggccgagcatctcaagagcatggtgcgcgagggggttcgagctcctcggcgc
cttcaactggtccgaccacctcccctggctcgcccacctgtacgacccaagcaacgtcacccgccggtgcgccgcgctcgtgccgcgcgtc
cagaccttcgtccgtggcgtcatcgacgagcaccggcgccgccgccaaaactccgccgccctcaacgacaatgctgacttcgtcgacgtgc
tcctctcccctcgagggtgacgagaagctcggcgacgacgacatggtcgccatcctctgggtaaagttcaaatcgatcgctttcctagcttgttta
actgcgcatacttctcagttctcaactgcgcatacctgtcggttctacagttttgtgtcgggctgtcggttgttcccggaagggaaaaaaaagaac
aaagctctgtcgctgaaaaaacatactgtacatgcatataatttgtttttgcaggagatggtcttccgcggtacggacacgacggcgcttctga
ccgagtggtgcatggcggagctggtgcgccacccggcggtgcaggcgagggtgcgcgccgaggtcgacgcggctgtcggtgccggagg
ttgccccaccgacgccgacgtggcgcgcatgccgtacctgcaggcggttgtgaaggagacgctgcgcgcccacccgcctggcccgctgct
gagctgggctcgcctcgccaccgccgacgtgccactctgcaacggcatggtggtcccggctggcaccacggcgatggtgaatatgtgggcc
ataacccacgatgccgccgtgtgggccgacccggacgcgttcgcgccggagcggttcctgccctccgagggcggcgccgacgtggacgt
ccgcggcgtcgacctccgcctggccccgttcggcgccgggcgtcgcgtctgccccggcaagaacctgggcctcaccaccgtgggcctctg
ggttgcccgcctcgtgcacgccttccagtgggccctgcctgacggcgcggcggccgtttgcctcgacgaggtcctcaagctctccctggagat
gaagacgccgctcgtcgccgcagccatcccccgcaccgc

FIG. 5

SEQUENCE LISTING

<160> NUMBER OF SEQ ID NOS: 21

<210> SEQ ID NO 1
<211> LENGTH: 2101
<212> TYPE: DNA
<213> ORGANISM: Artificial Sequence
<220> FEATURE:
<223> OTHER INFORMATION: GA2 oxidase promoter derived from GRMZM2G031724

<400> SEQUENCE: 1

| | | | | | |
|---|---|---|---|---|---|
| ggggacaaact | ttgtatagaa | aagttgccga | ggattgcagc | tcctggatca | tatcagaatg | 60 |
| tctgtcgctc | gccaccccgg | gcgcactgca | ttatatttct | ggcaggtgcg | caatacaata | 120 |
| tggcatgggg | ggcacgtagt | acggtactgc | cgtacagctg | cgtcagcaaa | tgccaacttg | 180 |
| tgtggtacag | ctataatcta | tagaaaaaag | aatattatag | aagtagtaga | agttggcgcg | 240 |
| tatggattaa | ggaaggtttg | gtttctagtg | actaatttag | tctctctatt | ttattcaatt | 300 |
| ttgttcctaa | attatcaaac | taaatgaag | ttttgttttt | tttatatagg | ataatttaga | 360 |
| gactaaaata | gaataaaaat | gaatggatga | aaaattagtt | cctaccaacc | aaacacccct | 420 |
| taagagctac | ttcgagaacc | tcaaatctcc | ttcgagactg | gaggagatga | aggtaaaaat | 480 |
| aaactaattt | tcccttcaat | cctttaatt | cacaaggggg | tgcgggtacg | gaaatgttta | 540 |
| ctactatact | ggaaaggtgt | ctgaaaccgg | gagaaaagct | ttgaccaggg | tggacctgtt | 600 |
| tatgggatcg | aagcggccgt | tgccccaact | ggcgactggc | gagccaccat | tgcgcggacc | 660 |
| cgagattaac | tatactacag | gagtactgtc | gggttggtac | caatacgtgg | cttgggcaaa | 720 |
| aagtctggca | ggcgccgctg | cttgtctgcg | gtttctatgt | gccgatgcca | tcgcaccgga | 780 |
| ccggatcggg | atgggatcag | cggaacatgc | gagagcgagc | ctgcactgca | ctgcatggcc | 840 |
| gcgaccgcgt | cgtccatcga | gccgcctatc | attagttggt | tccactgtct | cgccgccgaa | 900 |
| gcaaggcagc | acagcacaca | tcagcattgc | ttcccagttc | ccaatgcccc | gtcgtcctag | 960 |
| ccgaggcggg | ctcagtacca | acccagctga | aactacgaga | gatgcgctgt | gggcaggaca | 1020 |
| gtggtcgagc | gaggagtgta | cctgtagtta | acgaggattt | tattttacta | gtgcgtacgt | 1080 |
| acgtactgta | cgtactatga | tctctcacgt | gctctggtct | tatcactcgc | ttgattatac | 1140 |
| tatgatcttt | ttttcccctcc | acctgctctg | gtcttatcgc | tggcacgtgc | ttttacacgg | 1200 |
| ccacttagga | ctactcacct | cgtctcgtca | tgcttatcta | cttcagagcg | tcacggacac | 1260 |
| agcaaggagg | agtacgcaca | cgcagcatgg | actgcctgga | gcggggtgtg | gtgcactaac | 1320 |
| gcccgcctaa | ttcccggagc | tgcctgtgcc | ttggacgccc | atctctggtt | tcgcggggag | 1380 |
| aataataata | atttaggcga | aacacgggaa | cgggtcgtga | ggaaaagcct | gacatgctgc | 1440 |
| attacggccg | gtgccgttcg | gacccccagtt | attgatgagc | cgagtcaccg | acctgccaag | 1500 |
| aaaaggatgc | cggatcaagg | gcaggttcac | ctcatcttag | cgcatgcaag | cgtcgtccct | 1560 |
| aaccaaaaca | tcatcttcat | gtctggccgc | ccgcgcagcg | gtcccagtgc | cggcgtggtt | 1620 |
| aacgggaggg | actgggactg | gcagggccgg | ctaatggccg | acgtgcagtc | gcctcgtatg | 1680 |
| cgtttcccgt | tgagccatgc | atgcagcaga | gcagcgcggg | cggccggtcc | tgccaccggt | 1740 |
| ggatcgcggc | cgggcacgtc | acggcccggt | ccccgactgc | tctggctcca | tcgccgccac | 1800 |
| catgcaccca | aagcgatcca | cccccgatgc | atccctttc | tctccctgtc | agctgggccc | 1860 |
| atctcgcgtc | accgtagcca | ggtgccgccc | cgtcgcccg | ccccccgatc | tatatatgct | 1920 |
| gcccacgggc | tctcccactt | ctcccccaca | tgcacttgct | gcagcagccg | taggacacac | 1980 |
| gcacaccgcc | tcgacctcga | gtccaccact | gactccacca | cctcccccctg | ttttttttcg | 2040 |

```
acctcgctct gctcatccgc acggccagac agccgcaagt ttgtacaaaa aagcagtccc    2100
c                                                                    2101
```

<210> SEQ ID NO 2
<211> LENGTH: 1895
<212> TYPE: DNA
<213> ORGANISM: Artificial Sequence
<220> FEATURE:
<223> OTHER INFORMATION: KLU sequence fused with attB1 and attB2 sites

<400> SEQUENCE: 2

```
ggggacaagt tgtacaaaa aagcaggctc catggcgatg gcctccgcgg cttgctcatg      60
cacggacggc acgtggtggg tgtacgcgct cccggcgctg ctcggctccg acaccctgtg    120
cgcccacccg gccctcctgg ctggcctgat ctttctggcc accgtctcgg tggctctgct    180
ggcgtgggcc acgtcgccgg gcggtccggc gtggacgaac ggccgcggcc gcctcggcgt    240
cactcctatc gtgggacccc gtggtctgcc cgtgttcggc agcatcttcg cgctgtcccg    300
cgggctgccg caccgcgccc tcgccgagat ggcccgcgcc gcagggcccc gggccaagga    360
gctcatggcg ttctccgtcg gtgacacgcc cgcggtcgtg tcgtcctgcc cggccacggc    420
acgtgaggtg ctcgcgcacc cgtcattcgc cgaccgccct gtgaagcggt cggcccggga    480
gctcatgttc gcgcgtgcca tcgggttcgc gcccaacggc gagtactggc gccgcctccg    540
ccgcgtcgcg tccacgcacc tattctcccc gcgccgggtc gcctcgcacg agccgggacg    600
ccaaggtgac gcggaggcca tgctccgctc atcgccgcc gaacagtcgg cctctggcgc    660
cgtcgccctc cgcccgcacc tccaggccgc cgctctcaac aacatcatgg gcagcgtctt    720
cggcacgcgg tacgacgtca catcaggcgc cggcgccgcg gaggccgagc atctcaagag    780
catggtgcgc gaggggttcg agctcctcgg cgccttcaac tggtccgacc acctcccctg    840
gctcgcccac ctgtacgacc caagcaacgt caccccgccgg tgcgccgcgc tcgtgccgcg    900
cgtccagacc ttcgtccgtg gcgtcatcga cgagcaccgg cgccgccgcc aaaactccgc    960
cgccctcaac gacaatgctg acttcgtcga cgtgctcctc ccctcgagg gtgacgagaa   1020
gctcggcgac gacgacatgg tcgccatcct ctgggtaaag ttcaaatcga tcgctttcct   1080
agcttgttta actgcgcata cttctcagtt ctcaactgcg catacctgtc ggttctacag   1140
ttttgtgtcg ggctgtcggt tgttcccgga agggaaaaaa agaacaaag ctctgtcgct   1200
gaaaaaaaca tactgtacat gcatataatt tgtttttgca ggagatggtc ttccgcggta   1260
cggacacgac ggcgcttctg accgagtggt gcatggcgga gctggtgcgc cacccggcgg   1320
tgcaggcgag ggtgcgcgcc gaggtcgacg cggctgtcgg tgccggaggt tgccccaccg   1380
acgccgacgt ggcgcgcatg ccgtacctgc aggcggttgt gaaggagacg ctgcgcgccc   1440
acccgcctgg ccccgctgctg agctgggctc gcctcgccac cgccgacgtg ccactctgca   1500
acggcatggt ggtcccggct ggcaccacgg cgatggtgaa tatgtgggcc ataacccacg   1560
atgccgccgt gtgggccgac ccggacgcgt tcgcgccgga gcggttcctg ccctccgagg   1620
gcggcgccga cgtggacgtc cgcggcgtcg acctccgcct ggccccgttc ggcgccgggc   1680
gtcgcgtctg ccccggcaag aacctggggcc tcaccaccgt gggcctctgg gttgcccgcc   1740
tcgtgcacgc cttccagtgg gccctgcctg acggcgcggc ggccgtttgc ctcgacgagg   1800
tcctcaagct ctccctggag atgaagacgc gctcgtcgc cgcagccatc ccccgcaccg   1860
cctgagaccc agctttcttg tacaaagtgg tcccc                              1895
```

<210> SEQ ID NO 3
<211> LENGTH: 3926
<212> TYPE: DNA
<213> ORGANISM: Artificial Sequence
<220> FEATURE:
<223> OTHER INFORMATION: Chimeric gene "GA2 oxidase promoter
      (GRMZM2G031724) operably linked to the KLU gene (GRMZM2G167986)

<400> SEQUENCE: 3

```
caactttgta tagaaaagtt gccgaggatt gcagctcctg gatcatatca gaatgtctgt      60
cgctcgccac cccgggcgca ctgcattata tttctggcag gtgcgcaata caatatggca     120
tgggggggcac gtagtacggt actgccgtac agctgcgtca gcaaatgcca acttgtgtgg    180
tacagctata atctatagaa aaagaatat  tatagaagta gtagaagttg gcgcgtatgg     240
attaaggaag gtttggtttc tagtgactaa tttagtctct ctattttatt caattttgtt     300
cctaaattat caaactaaaa tgaagttttg ttttttttat ataggataat ttagagacta     360
aaatagaata aaaatgaatg gatgaaaaat tagttcctac caaccaaaca ccccttaaga     420
gctacttcga gaacctcaaa tctccttcga gactggagga gatgaaggta aaaataaact     480
aattttccct tcaatccttt taattcacaa ggggtgcgg  gtacgaaat  gtttactact     540
atactggaaa ggtgtctgaa accgggagaa aagctttgac cagggtggac ctgtttatgg     600
gatcgaagcg gccgttgccc caactggcga ctggcgagcc accattgcgc ggacccgaga     660
ttaactatac tacaggagta ctgtcgggtt ggtaccaata cgtggcttgg gcaaaaagtc     720
tggcaggcgc cgctgcttgt ctgccggttt  tatgtgccga tgccatcgca ccggaccgga    780
tcgggatggg atcagcggaa catgcgagag cgagcctgca ctgcactgca tggccgcgac     840
cgcgtcgtcc atcgagccgc ctatcattag ttggttccac tgtctcgccg ccgaagcaag     900
gcagcacagc acacatcagc attgcttccc agttcccaat gccccgtcgt cctagccgag     960
gcgggctcag taccaaccca gctgaaacta cgagagatgc gctgtgggca ggacagtggt    1020
cgagcgagga gtgtacctgt agttaacgag gattttattt tactagtgcg tacgtacgta    1080
ctgtacgtac tatgatctct cacgtgctct ggtcttatca ctcgcttgat tatactatga    1140
tcttttttc  cctccacctg ctctggtctt atcgctggca cgtgctttta cacggccact    1200
taggactact cacctcgtct cgtcatgctt atctacttca gagcgtcacg gacacagcaa    1260
ggaggagtac gcacacgcag catggactgc ctggagcggg gtgtggtgca ctaacgcccg    1320
cctaattccc ggagctgcct gtgccttgga cgcccatctc tggtttcgcg gggagaataa    1380
taataattta ggcgaaacac gggaacgggt cgtgaggaaa agcctgacat gctgcattac    1440
ggccggtgcc gttcggaccc cagttattga tgagccgagt caccgacctg ccaagaaaag    1500
gatgccggat caaggcaggt tcacctcat  cttagcgcat gcaagcgtcg tccctaacca    1560
aaacatcatc ttcatgtctg gccgcccgcg cagcggtccc agtgccggcg tggttaacgg    1620
gagggactgg gactggcagg gccggctaat ggccgacgtg cagtcgcctc gtatgcgttt    1680
cccgttgagc catgcatgca gcagagcagc gcggcggcc  ggtcctgcca ccggtggatc    1740
gcggccgggc acgtcacggc ccggtccccg actgctctgg ctccatcgcc gccaccatgc    1800
acccaaagcg atccaccccc gatgcatccc ttttctctcc ctgtcagctg ggcccatctc    1860
gcgtcaccgt agccaggtgc cgccccgtcg cccgccccc  cgatctatat atgctgccca    1920
cgggctctcc cacttctccc ccacatgcac ttgctgcagc agccgtagga cacacgcaca    1980
ccgcctcgac ctcgagtcca ccactgactc caccacctcc ccctgttttt tttcgacctc    2040
```

```
gctctgctca tccgcacggc cagacagccg caagtttgta caaaaaagca ggctccatgg    2100
cgatggcctc cgcggcttgc tcatgcacgg acggcacgtg gtgggtgtac gcgctcccgg    2160
cgctgctcgg ctccgacacc ctgtgcgccc acccggccct cctggctggc ctgatctttc    2220
tggccaccgt ctcggtggct ctgctggcgt gggccacgtc gccgggcggt ccggcgtgga    2280
cgaacggccg cggccgcctc ggcgtcactc ctatcgtggg accccgtggt ctgcccgtgt    2340
tcggcagcat cttcgcgctg tcccgcgggc tgccgcaccg cgcctcgcc gagatggccc     2400 gcgccgcagg gccccgggcc aaggagctca tggcgttctc cgtcggtgac acgcccgcgg    2460
tcgtgtcgtc ctgcccggcc acggcacgtg aggtgctcgc gcaccgtca ttcgccgacc     2520 gccctgtgaa gcggtcggcc cgggagctca tgttcgcgcg tgccatcggg ttcgcgccca    2580
acggcgagta ctggcgccgc ctccgccgcg tcgtccac gcacctattc tccccgcgcc      2640
gggtcgcctc gcacgagccg ggacgccaag gtgacgcgga ggccatgctc cgctccatcg    2700
ccgccgaaca gtcggcctct ggcgccgtcg ccctccgccc gcacctccag gccgccgctc    2760
tcaacaacat catgggcagc gtcttcggca cgcggtacga cgtcacatca ggcgccggcg    2820
ccgcggaggc cgagcatctc aagagcatgg tgcgcgaggg gttcgagctc ctcggcgcct    2880
tcaactggtc cgaccacctc ccctggctcg cccacctgta cgacccaagc aacgtcaccc    2940
gccggtgcgc cgcgctcgtg ccgcgcgtcc agaccttcgt ccgtggcgtc atcgacgagc    3000
accggcgccg ccgccaaaac tccgccgccc tcaacgacaa tgctgacttc gtcgacgtgc    3060
tcctctccct cgagggtgac gagaagctcg gcgacgacga catggtcgcc atcctctggg    3120
taaagttcaa atcgatcgct ttcctagctt gtttaactgc gcatacttct cagttctcaa    3180
ctgcgcatac ctgtcggttc tacagttttg tgtcgggctg tcggttgttc ccggaaggga    3240 aaaaaagaa caaagctctg tcgctgaaaa aaacatactg tacatgcata taatttgttt     3300
ttgcaggaga tggtcttccg cggtacggac acgacggcgc ttctgaccga gtggtgcatg    3360
gcggagctgg tgccgcaccc ggcggtgcag gcgagggtgc gcgccgaggt cgacgcggct    3420
gtcggtgccg gaggttgccc caccgacgcc gacgtggcgc gcatgccgta cctgcaggcg    3480
gttgtgaagg agacgctgcg cgcccacccg cctggcccgc tgctgagctg gctcgcctc    3540 gccaccgccg acgtgccact ctgcaacggc atggtggtcc cggctggcac cacggcgatg    3600
gtgaatatgt gggccataac ccacgatgcc gccgtgtggg ccgacccgga cgcgttcgcg    3660
ccggagcggt tcctgccctc cgagggcggc gccgacgtgg acgtccgcgg cgtcgacctc    3720
cgcctggccc cgttcggcgc cgggcgtcgc gtctgccccg gcaagaacct gggcctcacc    3780
accgtgggcc tctgggttgc ccgcctcgtg cacgccttcc agtgggccct gcctgacggc    3840
gcggcggccg tttgcctcga cgaggtcctc aagctctccc tggagatgaa gacgccgctc    3900
gtcgccgcag ccatcccccg caccgc                                       3926

<210> SEQ ID NO 4
<211> LENGTH: 2489
<212> TYPE: DNA
<213> ORGANISM: Zea mays

<400> SEQUENCE: 4
tatattttat gctctaaatt agattttttg tgacggctca cgagtcggct tgcgagccct     60
aagccgagcc tgattttga gcttgcaata cgaccgagtc gagccgagcc tggctcacta     120
ggtaatcgaa tcgcaccgag tcgatccagc cctagtttaa atgcactgga gctaatagtt    180
agctggctaa aaatagctag gtttagttag gttgaaccag ctaataaact aataaatagt    240
```

```
tgatggtgca gctaatagtt agttatacta ttagctagag tgttgggatg tctccagcta    300
aaagcatcta atagttaaac tattagctaa gctatttaga tttcttagtt tagatatctt    360
ccgatgatct tagcaactaa atattaactc tagtttattc aagcggggcc taaaacctct    420
aaaattaata gttagctact aaaattagct aggcaaattc taaacatccc tagttaatac    480
tttaactaat tgttaactag tttacggcta actattagtt agtttattag atggctcaac    540
ctagccaaca atttgttagc cgacaaacta ttagctatag agaaaccaga ggtcttatgg    600
ggtgtttggt ttctaggact aattttttagt ctattcgttt tattctatttt tattgactaa    660
attgccaaat acagaaacta atattttcat atttattaat ctagagatta aaatagaata    720
aaatagagag actaaaaaat agtctataga aaccaaacag cccccttacat gttgaatcag    780
gggttgtttg gttcatgggg actaaacttt agtctctccc ttttagtcta ttttagtcca    840
taaattacta aatataggaa ataaaaggga atagatcaga tttcctccct atctttagtc    900
ctattttttgg taatttaggg actaaaaaag agagactaaa gtttagtctc atggaaccaa    960
acatgccttc attcggccag acaactataa atggaaatac aaaaagtact gaacacaaga   1020
acgcttcagc aaagatggac aaacaaaaac cctgcccttg ttatatttgg gcagatagga   1080
tgcgtcgttg ctatatttgg atagctcttt gtctctgtta ccaaatttgg cccaggccaa   1140
cgtactactc tccagtccat tcctcaattc agacattcgt tgcgtcagta cgagaaacag   1200
tgaaaaaaat cgcataccat aaatagaaag cacccataat aacattcata cagcatcaac   1260
atcaagagcc aaatacagga aattaaagct ctctctagct agctagtacc acagctactg   1320
tacacttgca ttggcaccac gaagcatggg aagaggaaga atccaaccga acagagagca   1380
cacctgtccc cgtatggcag tatccatcca accctaccca cctaccccta ctgtcctaca   1440
tagcaagccg tacggccagc ccttcttact ggtccgtgaa gcaatcagta ctggtggcct   1500
ccagtgatct ccggagggcg gggggcacac accagagcag cggtgttggg gccggtctat   1560
ggcagagaga ggcatctgcg cgtacgaacc taccagctct cgacaggttg cgggtgacta   1620
gatgcggaag gggtccaggc ggttgtctcc gagccgcgag cggtaggcag ccttcttgta   1680
gtcgccccat gtgaagtccc tgtacaggct ctgcttgccg tgcccagca gctgcggcaa   1740
tggcgcgatc cgctgcgccg gcgccggtcc cgcgaagtag atcatggaca cccgcggctt   1800
caggctgttg gccaccaccc ggtgccgcac acttttcagc ctcccattcg tcaggaccta   1860
ttatcgcacg cacgagacgt acaaacccgg tcaattatat tcattgcctg ctgcatctgc   1920
atcgccgtc gtgtcgtctc ggcgcggccg gcgacccatg catgccatga gcaaaccacg   1980
ccttggcagg tacgtacgga tgatatgcgt atgtgcgcgc gcccgcaatg taacgtgcta   2040
cgggttatat tatacctgca gcgagtcgcc gacgatgacg aagaaggcgt cgcggtcggg   2100
aggcacgggc acccagcgcc cgtcgtcgcc gtggagcgcc agctgcaggc cgggcgtgcc   2160
gttggagcgc agcacggaca ccagctgcgg gtccgtgtgc tcgccgaagc cggtgacgcc   2220
gcacgagtcc ggcaggcgct gcagcagcgg gcacgcaggg tagtggttga tccggaacac   2280
ctggtcgctc gccgcgtccg ccaccatgcc gctcagcgcg tccctcggcg ccacgccgag   2340
cccctccgcc accgcctcca gcaccgacgt cgccaggccc tcacggagg ccacgtactg   2400
gttcaccgcg tccctgcacg ccggaccgga cctacccatc gttagaaacg cacgcgcgtg   2460
gggcgcaata atggcttcgc tgacactgc                                     2489
```

<210> SEQ ID NO 5

<211> LENGTH: 2507
<212> TYPE: DNA
<213> ORGANISM: Zea mays

<400> SEQUENCE: 5

| | | | | | |
|---|---|---|---|---|---|
| aaaaaagata | gtttattcaa | gattcttact | cataattttt | caactttact | agtttttcta | 60 |
| gtaattaata | tgctagcttt | tatccatgac | tatgatagct | ttaggggat | gttcctgtac | 120 |
| agttcgtggt | agaattagta | ccctttgctg | tcatagtcag | gaaggcccc | catcaaataa | 180 |
| attgcgcaaa | tgcataacta | catggttttc | aagacaataa | ttatcgcaat | aatggcacaa | 240 |
| ttgatgccac | aatatgcagg | gcaatgatat | gttagttcca | acaattcaag | agcatacatg | 300 |
| gtagtagcta | gtttctaaag | caaaagaaaa | ggcacaaact | gatgggacat | aagaaacttg | 360 |
| acagctccgc | agaatggtct | tggacgattt | tctgatgaaa | gtttggtata | attgccttgc | 420 |
| caaaagaaca | ttcgaaaggc | ttgcaatcgg | ctgctatcat | tttgcattga | aaaatggctt | 480 |
| aaacattttg | cttgtgatag | ggaagccctt | gtccatgcat | gctgggaaaa | acattgaaat | 540 |
| gcctaacagt | tcttttttt | gtgaccgagt | aaattcttaa | taacaattga | ctgaacataa | 600 |
| cagatgagat | atcttaaca | caccacacag | gccacaggca | tgcagtggcc | taattcaata | 660 |
| gagttggctg | agagcaaata | aaatgaaagg | gacaagaaaa | ccctcctctc | tcgctctaag | 720 |
| gtagttagaa | gaccatctcg | gtgtcaggtc | cctctccaac | aaactatata | tgtgtatttt | 780 |
| gcatgtcaat | cagtctcaca | tatctgcggt | gcagtggtct | tcaattaatg | gccgtaccca | 840 |
| accaccaatt | gatgcggcta | gcaacagaac | ccatggctat | tggatagctc | ttacagcttt | 900 |
| ttttcagcca | agtacactaa | gttccataca | gaaaacgatg | ttttagatg | gccacacagg | 960 |
| atgtacatca | catacatgaa | cttcgaaatg | aactcccttt | gttctctgtc | aactagtcat | 1020 |
| gaatcattaa | tatattgcca | gtgttccaat | actcataatg | tagcaccaaa | ctaattaaga | 1080 |
| agtaggaggt | tgttcattgc | cttgatcaca | ttaatataat | tgtaaaatgc | ttggcaacaa | 1140 |
| gaacaaaaac | agaaatggca | tcagaatctt | tgcagtagcc | attttgccat | ggaacacaca | 1200 |
| cacacacaca | ggtataggta | acagcaagta | gggtccacag | aagtacaaaa | gcttgatagg | 1260 |
| aaataaaatg | ctccccaggg | ccccctaaag | agcatatcca | tgctatccat | ataaagccaa | 1320 |
| gcaattgaaa | aggaggcaca | catgcaacgg | gtcctctta | tggcaagatg | aatgagatgt | 1380 |
| cccggaggag | ggaggtggga | gtggcagcag | ggcagtgat | gagtgattcc | aaacactgat | 1440 |
| gggtctatcc | atggagcagt | ggaaagagca | tgcccaatcc | tgtcgagaga | aacccatttg | 1500 |
| cccgctggaa | aatcggtgac | accaagctat | ccatgcatgc | atcacaagaa | cctatagcat | 1560 |
| gtgactggat | tctgcttctg | ctgcatagcc | cagcagatgc | atcaagcagc | taccgtcttt | 1620 |
| tcaatgctgc | agcttttgag | ttatgctgca | tattcatata | tacgtcaatc | agtcaaaacc | 1680 |
| ttctcatctt | tcttctgtct | cctttttttc | tctgtcatgg | gctcatggca | cacatccaac | 1740 |
| tggtcttcgt | gataaatcca | ttcttttgat | ccaattggtc | ttctcacatg | ctgatgcttt | 1800 |
| tttttttttc | cttcactgtt | gctgcagcaa | tgtggtgaac | gagtatgtgg | gagcgatgag | 1860 |
| gcagctcgca | tgtgagatcc | tggacctgct | cggagagggg | ctagggctca | aggaccccag | 1920 |
| atccttcagc | aggctcatcg | ctgacacaga | cagcgactca | ctcctgcgga | taaccacta | 1980 |
| ccctccacca | tgcgccattc | acaagcttga | ccacgacagt | cagtgcagga | tgaagaacag | 2040 |
| tttcaggatc | gtggcaggca | atggcgcgaa | ccagtcggca | ggtgcacgga | tcggattcgg | 2100 |
| ggagcactca | gacccgcaga | tcctttagctt | gctccgatca | aacgatgttg | acggccttca | 2160 |
| ggtgcttctg | aacagcgacg | gcagagaggt | gtgggttcag | gtgccagccg | atccatcagc | 2220 |

| | | |
|---|---|---|
| gttctttgtc aatgttggtg atctcctcca ggtaaaataa acaggcactg cggctagtag | 2280 | |
| attaggtaaa tgagaattgc ttctatatat gagctaccaa cgactgtgtc ttctaaacag | 2340 | |
| acaaccaggt taattagcaa ttgctccttt ttttgtgaaa agatgggtca gcactgatgt | 2400 | |
| tttttggaca gcatatgcac caagtacatc gtaccaactg acaaggattt ctgttttgt | 2460 | |
| cttgttagtt gttaccacat ctgaatctaa caacattaat ccattcc | 2507 | |

<210> SEQ ID NO 6
<211> LENGTH: 2404
<212> TYPE: DNA
<213> ORGANISM: Zea mays

<400> SEQUENCE: 6

| | | |
|---|---|---|
| aaccaccaag actttgttga tgaactcaga aatgttaggt tcacagtgag tactgatgga | 60 | |
| atgaatctat ttgctgagaa gagcagcaag catagcacat gaccggtgat cctcaccatc | 120 | |
| tacaaccttc ctccatgatt gatgtagaaa cgaaagtata ttttgttaac catccttatt | 180 | |
| tttggaccta cataaccttg agttgacata gatgtatttt tggagcccctt aatggaggat | 240 | |
| ataaaaatat tgtaggaaac atgtgttcaa atgttggatg agtatcgtaa agattcattc | 300 | |
| atgttgaggg caattctttt tgttatgatc aacgattacc cttctttctt cacattatca | 360 | |
| agccagttta agggaaaggt tggttccaca gtatgcattg atggaactgc ttacgtgtcc | 420 | |
| ctttctgcat ctaagaagat aatgtacatg aggcacatac gcttttttatt ggaatgacat | 480 | |
| aggtatcgca tgcaaaagat ggataagtac ttcgacaata atgatgaatt gcattccact | 540 | |
| gctccatcgg gtaacaataa aggtcaaaga gttttttaaaa tagtcacgaa tatcaaatttt | 600 | |
| gttttcagaa agaagacaaa agacagaaac aaaaggaagg atgccaaacc agctccgggg | 660 | |
| gctacattca ataagaagtc tattttcttc gactatttgc cttactagaa agagttagat | 720 | |
| gtgcggcaca cgatcgatgg tatgcatgtt cagaagaacg tgtttgaaaa cataattggc | 780 | |
| accttgctag acataaaggg caaaataaaa aaagggctca attcacgcat ggacttgata | 840 | |
| aatttagata taaaaaagaa cttgatcctg ttttttcaaga aaatgggaag tactatctca | 900 | |
| cagcagcaag ctacaatctc aatgtacatg agaaacatgc gatgtgtgtt tggctcaaga | 960 | |
| atttgaaaga cccatccaga ttttgctcta gcatacggag tatttgtatca atgaaagacc | 1020 | |
| taacagtcac caactacaac tcacatgatt gtcatgtcat gctgactaca ttcctgccta | 1080 | |
| ttgccatcag ggcaatgaat ccttttgttct taaagatgga aatcatacgg ttgtgctact | 1140 | |
| ttttcaacag gattccacaa aagataattg atcgtgatgg gttgacatct cttcaggaat | 1200 | |
| tcacagtggg gacaatatca cagttttaga tgtgtttttc tccatcattc tttgatatta | 1260 | |
| tgttgcacct tgtggtgcac ttggtgccac agatggaggc actgggtccc atatacttgc | 1320 | |
| atgaaatgta gacgtatgag cgtttcatgt taataatgaa tggctatgta tcagctcgtg | 1380 | |
| ctcgtcctga ggcatcaatg atagagggggg actgtaccga agaggccatt gagtccagag | 1440 | |
| gtccattctg caatagtatc ctaaaagatc aggttgcaaa atgcaataag tttgcctccg | 1500 | |
| tcacgcacacg agggtaaact gtatggaagt gggtggatga acataaatc tttcatccca | 1560 | |
| ccggattaca atacagtact tgaggcacat cacaacatca tacatcagct agcgataatg | 1620 | |
| gagtcatttta tgcaacaaca catcagtgag cttcgcgagc aaaatcatag gcataaggat | 1680 | |
| gattgggtaa tgaatcaaca caagcagtgg ttcaacacat gactaatggt gaaaaacatt | 1740 | |
| ccacatggag aaacaataga agaacaaacc atcaaggagt tgacatctag accttcacat | 1800 | |

-continued

| | |
|---|---|
| caggtcacga catggcaaac ccatgtcatt agtggattca catttcgcat caaaattgag | 1860 |
| atgatttaga tttgttagaa gctgccatac aagacttaag gaaataatga taaaataagt | 1920 |
| ctcgtgccaa tcttatattt tatagtttac agtgaagttg tagttggtgt atatctcagc | 1980 |
| accttatcat ctatccttatc ttgatttagc acctacttta gtagttagaa tgtgctaaaa | 2040 |
| cttggtttat aagtttttag aatatgctaa aacttacttg gtttataagt tatatgtatc | 2100 |
| taaccctgcc atgttttata tgttgtggct tataagaaat aaaagatctg ttcaaaaagg | 2160 |
| tgtcactaac acgtataagg acaccgctac tctccccctca gctggctccc agcccactat | 2220 |
| acagtatata cacacatcat cccactcctt atcgctatat atagcagtgt tgtgtgtcca | 2280 |
| tctctctgct acattgcacc gcatcgtcta agctcgcctg ccctttacag cagcttacta | 2340 |
| ctacaaagac gacaacacag cgcgcgcgcg ccaagctgag ctcagctcgt cacgacacgc | 2400 |
| cagc | 2404 |

<210> SEQ ID NO 7
<211> LENGTH: 2500
<212> TYPE: DNA
<213> ORGANISM: Zea mays
<400> SEQUENCE: 7

| | |
|---|---|
| gatgatgagc aggggcgtcg gcgtggtaag ctctcgcgag agagagagaa tagggcatgt | 60 |
| ggttgggtga gctcggaggc aagggaaccg cctccatggg ggcgcaacta gaatttatac | 120 |
| ggaggagggg agtgtagagg ttgtcggggg gagagggaga gccggtcgac agccattaat | 180 |
| ggcggcggtt acctccttca atggagagat gaggagagtg ggagtgaatg gagagggtgt | 240 |
| cggttttggg tgtagggaac cgagtggtcg gatgaggagg cgagggaggg ggcgagaaag | 300 |
| ggatgcgaca ggtgagccag cgcggtcgag catggatgcc gatgaggccg gcggcaagg | 360 |
| gcacacgcgg gacgcgcgcg cgtccgcacg gtgtgggaag gggaaggacc gcaaagacgg | 420 |
| acccgcctgt aagggctgat ttggtgatta gggatcccga ggggatccat ggggagaaat | 480 |
| ccccttgcaa ttcaattttg aataacaaga ggattttttct ccccatgaat catctcggga | 540 |
| tccccgatca ccaaatcaga cctaagtgag aaagggaggg gaaatgagag gaagagaggc | 600 |
| gcagctgggc ccttggtggg ccgaattcag cggacgatta gggtttcaat tttttttctt | 660 |
| tttgcttttc tcttttttga ataggttatc cattaaaaat ataataatt atattttaa | 720 |
| atattttaaa cattataata aatctaataa taatatttat aattaaaata ccaaatattt | 780 |
| atctttagac caaagtctaa tatatttaaa atttggattt cgcataaacg aagactataa | 840 |
| ataaaatctt caacaatgat ttgcaaacaa aattcatgcc ccatgaatga atgaatatga | 900 |
| aattaaacac tttgttcaaa ttttaatata ctctctacta agtttaacaa ctactaatac | 960 |
| attattttaa ttgaaggatt taaggtgtta cactcaagag gctcaacggg aaaggcacgg | 1020 |
| gaagaagaga atgaatgaga aagccttgag aaaggctaaa gttacaaccg gtattaaaga | 1080 |
| cttaagggta gggtgtaaac gaatccgata cggatggata ttactccttc tatatttatt | 1140 |
| ttcatatttt ctctttagat tcgaaacaaa tttggatatt atcaagttgt gtcgaataag | 1200 |
| atttgaatga atatcgatat ttcaaatatc caactttaag aaaacggata tggataaaga | 1260 |
| acagatttaa tctgaaactg agtacctaga ctcggataca gatcggttct catctctctt | 1320 |
| agacgaattg aaattaaata cgaatgtata atatcagtac catttatatt cctactagta | 1380 |
| agctagaact gaaagttctg ggatggaacc aaagttacaa agaggcattt tagacttttt | 1440 |
| agtgtcggtt cgtacgaaca aggcttcaga agaaaaaaaa acctttaata tctgttcttt | 1500 |

```
taaggaacgt ctttaatcaa tgctaattat ttaaccgtat gtagtaacag gtaggtgatg    1560
aaatggaaat gtcgatgcac gctacggcgg ccagcacatt caggcaagaa gcagacaatg    1620
tttctctttc tgggcggtgc acgttcctga tgctccaacg gtgagttttc cgttttgggc    1680
actggcatca tctgccgata caagacatgc atgcatggtc gatgaaccag gtgctgtcag    1740
aatgaactta actaaacaaa gacgactaaa ctaattcagg acggcaatgc atcgagctgt    1800
actgaatgga acgcttttgc accctccggg agcatcggat cctctgtgcc acactatgct    1860
gtgtgctgtt ccactgctca attggacgat gacgacgatc tagcgcgctc gctgctttcc    1920
tctaatcctc taaccatcta taattacttt ttatctttaa ctattaaata tattagatgt    1980
caagagctgg tattattcta accatctagt atttaaaatg cacatcacca ggtggggcgg    2040
aaaggttgtc accaggcccc tcatcaacat gacaaccaca gaagatctgc tctcccgtac    2100
ccaacacagg cccagcaaat aaaattacat cgcggcctgc aattccaaga aaagggaggg    2160
atcggccgcc agctgcttcg ttgaatcatc cgtagcaaat actactaata actcgaggcc    2220
aggacaccag gtcaaaacca gaacaaactg tcagcattcc aagcggaatc ttcaactcca    2280
cccccaccgt gtaccattta tacgtgcgct gcccgcggct gccacaccca cacccccgacc    2340 ggccggccgg cggcatcatc atcctcactg ccactctaaa actctctctc gcgcgcgcgc    2400
gcgctccaca gtacgcaac acggtacacg tgcaatcata ttcataccac gcaataatca    2460
tctagccatg gtagcgccgt cggcggcggc aggccgggac                          2500

<210> SEQ ID NO 8
<211> LENGTH: 2494
<212> TYPE: DNA
<213> ORGANISM: Zea mays

<400> SEQUENCE: 8
cttccatcca cggcgacgct ctgccccgc acctcacgcc gctcacaacc atgtcaagac      60
gggccatgcc ctggtagccg cgcctaggcg agctgtgcct gaatacccgt agaatttag    120 tccctacgat cccctactat ctctacaatg gacgtgttct cttgtgcat tgataaaact    180 agcctttta cattatatat ttagcatgcg taagataaaa ttagtataag ctatttttc    240 ggatttattc catactacat ccctatctat ctatgaagac aaaaagaat ttgattaaaa    300 tgcattccca gtcttccata tattgtgtcg cttgatccct aaactctcaa accataaaa    360 gcgagtacta aaaattggcc gaaccatcca aaatatatat gagcatctac gtcggtggaa    420
tttagataga ccggtcattt ccccgatttc tagagtttag aaattcaata acataaccgt    480
aaacgccccg gcagctgcgt taggtcacgc cgctcacaac catgaaccat gtcaagacgg    540
gccatgccct ggtacggtgg ccgtgcctag gcaagctgtg cctgaatacc cgtggaatt    600 ggatagtcca atccggatt agatggaccg gccaagtttt agtgtccatt tttctgattt    660
ctagagttta gaaatccaat aacataacat atcaagttca aggaccacaa atatatttt    720 tacttaataa ttacatatgc aatagatcta ctattattat aactatcaac atgagaattc    780
atatgactta caaaaaaaaa tactagaatc ataagattta tttacaagtt gtacctcatg    840
gtaacttgac tatctgtaat acttttatgg tgtgataact tggtacccct atagacaatg    900
aattttgacc atattactga ttttttatagc gacacattgt aaaatagcaa gcaagatctc    960
aaggaaatca aaactagatg caatcaccct tttgggctaa atgcaacaat aatgatgta    1020 gtgctctcat atacagagga gatgattttt atcctagttg gaaacaactt tagaaaaaca    1080
```

```
tttagtaagt tccctactta aaccccgatt aaaaataaac caattcggaa tctacgaaaa    1140
tcggcctaat tagctttgaa actcggtttg gccgaatttt tgtagtgtag ccggcctgac    1200
aatagaaggt ggacttgtct gccatgcgag accgtgtgac tgactttaac gactcaatgt    1260
ttagttgttg acatgatgtg cttctatgtt cggacacttt tgagtgtca gccgagcggg    1320 aatggttgct ccagcgtcca gcgtcccgag cacaggccgt tcttgcccaa cctggtgcgc    1380
cggccccatc agccatcaag cgaaacaggc cgttcttgcc caacctggtg cggcagctgt    1440
ggtgcagatc caatctacgt tttgttcgat tcagatgtgt attaaatcgt gatgtaacca    1500
ttatttagat tagaagagat ttttgttttc tgttttcaat agttttagcg acttatgaga    1560
aacttttttt ttgtatgctc aactgagcgc atataccgta gggaccgatg gacccggccg    1620
gagaggcaca acacatgatg acatgaccgc ctttctttcc gacgacacag ccgcctaatc    1680
tccggacctg ccttcgacgc cgatctctgg tctcagtggc tcacggcaac agggagaata    1740
atttagcgag acacgggaac gggtcgtgag gaaaaaaagc ctggcagcat catggccggt    1800
gccgttcgga ccccaggcat ggcagttatt gatgagccga gtcaccgacc tgccaagaaa    1860
ggataccgga tcaagggcag gtccatctca tcttagctat agctcagtca gacgtcgtcc    1920
ctaaccaaac atcatcttca ctgcctcact cttatctgaa cagtgaccag ccggctggga    1980 ctggacgag ggccggggcg ccgtgggaca cggctattgg ccgacgtgca atcgccgggc    2040
atgcgttccc cgttgagcca tgcatgcagc gcggccggcc ggtcctgcca ccggtggatc    2100
gcgtccggac acgtcacggc ccggccccgg actgccctgg ctccatcggc accatgcacc    2160
caaagcgatg caccccggcc ctgatgcatc attttcttct ccctgtcaga tgggacccca    2220
tcccggcacg gcagccagcc agccagccag gtcaggtgca gtcccttccc ttctcgcttc    2280
gcccccggct agacctcagg ctgatctata tatacacccc cacgagctct cccacttctc    2340
ccccccacat gcacttgctg caggagcagc cgtagtacac acgcacaccg cctcgactcg    2400
actcccacct cccctgttct caccgtgctt gccctgtttc gacctctgcc catccgcgct    2460
cgcgtgcccg ccgtacagta caggccagac agcc                               2494
```

<210> SEQ ID NO 9
<211> LENGTH: 2046
<212> TYPE: DNA
<213> ORGANISM: Zea mays

<400> SEQUENCE: 9

```
gaggattgca gctcctggat catatcagaa tgtctgtcgc tcgccacccc gggcgcactg     60
cattatattt ctggcaggtg cgcaatacaa tatggcatgg ggggcacgta gtacggtact    120
gccgtacagc tgcgtcagca aatgccaact tgtgtggtac agctataatc tatagaaaaa    180
agaatattat agaagtagta gaagttggcg cgtatggatt aaggaaggtt tggtttctag    240
tgactaattt agtctctcta ttttattcaa ttttgttcct aaattatcaa actaaaatga    300
agttttgttt tttttatata ggataattta gagactaaaa tagaataaaa atgaatggat    360
gaaaaattag ttcctaccaa ccaaacaccc cttaagagct acttcgagaa cctcaaatct    420
ccttcgagac tggaggagat gaaggtaaaa ataaactaat tttcccttca atccttttaa    480
ttcacaaggg ggtgcgggta cggaaatgtt tactactata ctggaaaggt gtctgaaacc    540
gggagaaaag ctttgaccag ggtggacctg tttatgggat cgaagcggcc gttgccccaa    600
ctggcgactg gcgagccacc attgcgcgga cccgagatta actatactac aggagtactg    660
tcgggttggt accaatacgt ggcttgggca aaaagtctgg caggcgccgc tgcttgtctg    720
```

```
cggtttctat gtgccgatgc catcgcaccg gaccggatcg ggatgggatc agcggaacat    780
gcgagagcga gcctgcactg cactgcatgg ccgcgaccgc gtcgtccatc gagccgccta    840
tcattagttg gttccactgt ctcgccgccg aagcaaggca gcacagcaca catcagcatt    900
gcttcccagt tcccaatgcc ccgtcgtcct agccgaggcg ggctcagtac caacccagct    960
gaaactacga gagatgcgct gtgggcagga cagtggtcga gcgaggagtg tacctgtagt    1020
taacgaggat tttattttac tagtgcgtac gtacgtactg tacgtactat gatctctcac    1080
gtgctctggt cttatcactc gcttgattat actatgatct ttttttccct ccacctgctc    1140
tggtcttatc gctggcacgt gcttttacac ggccacttag gactactcac ctcgtctcgt    1200
catgcttatc tacttcagag cgtcacggac acagcaagga ggagtacgca cacgcagcat    1260
ggactgcctg gagcggggtg tggtgcacta acgcccgcct aattcccgga gctgcctgtg    1320
ccttggacgc ccatctctgg tttcgcgggg agaataataa taatttaggc gaaacacggg    1380
aacgggtcgt gaggaaaagc ctgacatgct gcattacggc cggtgccgtt cggaccccag    1440
ttattgatga gccgagtcac cgacctgcca agaaaaggat gccggatcaa gggcaggttc    1500
acctcatctt agcgcatgca agcgtcgtcc ctaaccaaaa catcatcttc atgtctggcc    1560
gcccgcgcag cggtcccagt gccggcgtgg ttaacgggag ggactgggac tggcagggcc    1620
ggctaatggc cgacgtgcag tcgcctcgta tgcgtttccc gttgagccat gcatgcagca    1680
gagcagcgcg ggcggccggt cctgccaccg gtggatcgcg gccgggcacg tcacggcccg    1740
gtccccgact gctctggctc catcgccgcc accatgcacc caaagcgatc caccccgat    1800 gcatcccttt tctctccctg tcagctgggc ccatctcgcg tcaccgtagc caggtgccgc    1860
cccgtcgccc cgccccccga tctatatatg ctgcccacgg gctctcccac ttctccccca    1920
catgcacttg ctgcagcagc cgtaggacac acgcacaccg cctcgacctc gagtccacca    1980
ctgactccac cacctccccc tgttttttt cgacctcgct ctgctcatcc gcacggccag    2040
acagcc                                                              2046

<210> SEQ ID NO 10
<211> LENGTH: 2120
<212> TYPE: DNA
<213> ORGANISM: Zea mays

<400> SEQUENCE: 10
gacgaaactt acctctactg ctcttttcac gagcatggtc cctttcagtt ttctccctcc    60
aacgaccatc atatgtacaa cacaaaaagg ctatcacatc ctaaaacata catggtatta    120
gtaggatgaa aaatgtcata attgtgaata aataagatac ttgaaacatg atcgaagcga    180
agatgcactg gaacatactt ccctccagtc aacaaactct tttttgtaaa tgaagatcca    240
tctctgaatt ggcatatcta taaagctcca tctaactaaa ttggaatatc tagtctagaa    300
agctataaaa ttactctaac tgaacactca acgtctaaaa cagactccat cagactgcac    360
acaaaaaatt gagtgtacaa caacaaatgt atcggccaga tagaaaacat gattgaattt    420
catgcttaca taactatttc acagctcttg taagcaatga catagggcga aatcatgcaa    480
atcactaaac caaatcacag atctaggcat tttaggaaaa tacatgaaaa gcagagctac    540
ctttcgacga ttcaagcctt cttctacggt tggactgcag cctccacccg ccaacaacga    600
cggtgactca ggaaagctcc tccatcgctg gtgccaacct tctatcgaac gaccggatct    660
aggacggtgt ccaaatcgtc catgcccccg cgtgccgaga ctgttggagc taccccttcc    720
```

```
ctcgcagcca cactgacgcc ggacaccaag taactgcctc ctccttgctc accagttcac    780
tgacaatgcc ggtaatggta gaggaagagc aacgactgga tatgaggagt gccactcaca    840
ccacatttgc gatgaggagg gggcgagatc gagatgggat taaagggagg gggcggacct    900
tggcggcgat cttgggcggg agggcccggg taacgcgcga gcggggcagg gggagacgac    960
ggtcgtctca acgatgtgga ggatggacgc ggtgtctgtc ggagcaggtt gggggagtgg   1020
gtgcgtcgct ttcctcctcc aggcctccac cctcgctctc gctcgctcat cgctcgtcgt   1080
caccgccaca ccagcgggga gggggaaggc gagacgcggc gggctagggt ggcctagggt   1140
ttcccgtcct cgatattttt cagtggttgt aagagccgca gcgggggtgg cggcggggat   1200
ggctcctggg ctatccgcca gcggcgtcgt cgtgtaggtt tttaggtgtg tgtcggagca   1260
gggttggggg agcgggcatc gcgagcgggg cggacgcgac gtcggagga cggggcgcgg   1320
cacgcagggg aggaaggcga caatgtcggg atggcgggcg gggattgcgc ggatcgcggc   1380
ggccggcggg gattgcggcg cggggatcgc ggagggcgca tggcgggcg gcgggcgtc   1440
gggaggcggg ggcagtctac agtagggtct taatagttag tagagattag agtgcgggcc   1500
caaagcaccg cacgcacact gctcgcctat tcaaaaagct ctctcatgat cccacactga   1560
tggaggtcgc ctcgtcattg tacccttgca ggaatccgtc aacagaaaca ttatctgaga   1620
tgaacagcac ccggacgctt atcgccccgc cctccgaccc cactgcaccg gcggatcgcg   1680
tcgggacacg tcggcgatat ctcccccccg ggggccgtg cgtagggcgc cgctactgcc   1740
accacccacg aatcaagctc ggatctgccg cgctcgaccc aaatcaaaag gcccggccga   1800
gggggataaa aagttcagaa acacgcgcga tgcagaaata cagacaaaga aggtgggac   1860
ggggacgacg atgaacagct cgtaactaac gttgttcgct ccctcccgc tcgtttcgta   1920
tcgccgcgtg gggccccggc gccccgtccg tcctcctccc cctatataaa tacgcgccat   1980
gaagccttct tcgttcgcca ccacatgcac tcgagctcga gctccagtca ccagcggtga   2040
cacgagctcc gggcactcct ccacctgttc cgcttgttgc cgtacattgc tctgcttctt   2100
cttggcaata tatatatata                                               2120
```

<210> SEQ ID NO 11
<211> LENGTH: 2467
<212> TYPE: DNA
<213> ORGANISM: Zea mays

<400> SEQUENCE: 11

```
aacctgacat ctgctcaaaa gcggtcagga gaagtttcac atttcgtgct tgatccaagt     60
tatgatccag aaaaacaacg gtatcatccg cataccggag gatagaaagg ccaccatcca    120
ctagatgagg aaccacaccc gtgaattggt tatttacctt tgctcttaaa aatagaattg    180
gcaacatgtc cgcaactata ttaaagagaa tcggagagag aggatcacct tgacggagac    240
ccttatgagt agaaaagaaa gggccaattt catcattaac tttaacccccc acatgtcctc    300
cagagacaat tgactaaacc caatcacacc atttctgcga gaaacctttc attcgcatag    360
cttgttggag gaagggccat tttaccttat cataagcttt ttcaaaatcc aactttagaa    420
tcactccatt catttttttc ctatgaagtt catgtagatg gaatcaaatc tctgacactg    480
aatcaagtat tttaatttac taacaccatt ccctatatgc tcggcagttt gtccattaat    540
caagaacata ctctgggcaa gagttttttt ttttcttcca aaacaaaaa aaaaacaaca    600
tcagcccctg aagacaagga gcagtatata tatcgaataa tcgtgtgcaa acaggatgac    660
gcgaggccgg cgatgacgga ggatggattc gtaatcgtca tatacgcagg ccgaaccaac    720
```

```
ggtatggcgt gtattatata tatattctgg agaaagagga gcagccaact tttaagttca    780
caaaatattt catgctcgtt aaagagaaac agtgccatgc atgcgcggcg ttgtgtgcct    840
gtgtactagc tagttgatga cgaacctgca gttgcaatgc aaccaccacc aaatcaacta    900
gtctagctcc tcaagccacc atgccccac ctagccatgt gcccaaaaa ggagcagcat    960 caagccggga cggcatggcc ccttgtctac tcagggcacc gttatattat acgtatagct   1020
ttgtttctgt ggctctctcg gattaagcag cttcaaacac aacattcccc cttctttgtt   1080
tcttttatat ataatacagg ttgcgacaac acacaatcat atttaatagt attggtttgg   1140
gtagagtaga ccctaatata gcagtgcaat gattgagcca cacgacag cgagggtct    1200 agtaagctaa tatggtggac ccccacaaac atactcacga taaacaaatt taatatcaaa   1260
atgagcatat ggtacacata ctagatatta aacagacaag aacaaatatc ctactttatc   1320
ttagcgaaga gatcgagaaa ggtataagtt gaaaggagt ataaccctt tttatagctc    1380 gtccggtcgt tcgttcttct ttagttaacg ttgtggtact atatatgaga gcgctacgtt   1440
gtatacgact tcctgtcgtg ttgaacttga gtggttttc atggtccttc tgtatggtaa    1500
caaaccactg gtaaatgaga agtgagattg agagagagga acatatctac gccctattat   1560
gttgggcttg ggtggctttg gattggtttc tcagagtcca actgtgatgg gttaacaaac   1620
cactggtaga cgagaagcga aagaggaaaa aaaacagat gttgcaaaaa aaaatctgt    1680 acgtggttaa aaccggtgct ttaaaagagt agatatatat ttaaatttaa attaaataaa   1740
taataaacct cgatcgaccg accaatcgga atgcatccct actccggttt acgagcggcg   1800
agaatgtgcc acagacgaga cgacaggacc atgacatcac agcagggttt ggcaactgct   1860
gtagcaactg tggggcgcgc ccgtttgcct ccgatcaggg cggccatcat ctgctgctgg   1920
ggcgcaccgt cggggggtgtc tgacaacgct gtacaaccgc acccttagct tccagagaat   1980
tcaggcacgc tatattattt atcatggtcg taccgcactc tctagtctct acaccggtcc   2040
cgtactaaac tctagactgt ccacatcgct ggcctggtca aaacacgcgc gcgccgcgtc   2100
caagtgtcgg cctgcgccgg cgcgcctcga ctaaccacca tcagtagcgg ctaattaacg   2160
cgggagagat tcggccggac ccgtgcactg tagaagccat gcccacgagc gtacgtgcgt   2220
gcgtgcccaa gctgcgtgcg tgtacgggta cgatggtgca ggcatgcccg agcgagaacg   2280
tgcagccagc ccaagccacc cgtcgatgg ccactgctat atatatgcag cacgcggtcg    2340
cacaggcagg cagacaagca cacagctagg tagtcccca tcagctagag ctcagcttcc    2400
gcgtgcctgc actgcacata cgcacgcaca gctccagaca cagctacgac tcgaccacaa   2460
gccagcc                                                              2467
```

<210> SEQ ID NO 12
<211> LENGTH: 2456
<212> TYPE: DNA
<213> ORGANISM: Zea mays

<400> SEQUENCE: 12

```
ccaagaacga tggtttcctt cctaaaaatg ggggaagtct ttagggttga tttggtgacc     60
ggagatctca agggaaagaa atcctcttgc tattcaaaat tgaattgcaa gtggatttct    120
ctccatggat cccctaggga tccgtaatca ccaaatcagc ccttatagac cagatgcaaa    180
ccgagatttt tacaatacaa cccctcataa actaaagaat agatctcact tgcaagtcca    240
ccatcaattt cagaatggtg ttctggttct tgttgttgct gctgcatata gggtctacct    300
```

```
tcctgtttat gaggggccat aggaatcttg gtttgtatat agatatggta atgaatgacg    360
atccaaatat ttattcctaa attgttatga tcttaaatta ttttttgttt aaaaataaat    420
agaattagag tttgatcctt acattttata gtgtaaaatt taaagtctat tatcacttct    480
atttgtatct agactgtaga ctgtaggatg actgccgcgc gcacgcgtta cgatgtttgc    540
agttaagccc caaatcacaa acaagctgtt cggttggtct gctcttccgc tggtgctgtt    600
cggcttgctg atgttctata gccacggagc tgtaacattt ggttagaaca tgaaaaaccg    660
cctaaaacgg tcaccatcca tttggattca tcatacatgt cattaataag gtatgttcgt    720
ttccttagtg ctaaagctta gcacctgcta aaatttaaca tgtgtaggtt gtttggatga    780
agcgctaaac tttagcactt acggcccgcg aggagcacgt ggccaatggt gagcgaggga    840
gaaagaaagg gatattaaat gcaaaatatg gctggaggac cacttttagg tgatgtttgg    900
tttctaaaga ctaatttgta gtcactctat tttatcttgt tttattctct aaatcatcga    960
atacgaaaac taaaactcta ttttagtttc gcaatttagg gaataaaaat ggagagagta   1020
aaaattagtc tctataaacc aaacattccc ttagcacagt ttagcatatt tagtagaact   1080
aaagtgctaa ttagtgctaa actttagcgc ataatacttg tagtcatcat gtttatttct   1140
ttagtagcta ctaaaattta gcaaaaaatg cagcaagagg aaacaagtag tctctaagac   1200
agacatttat aaattctgcg tgtgtccttg gtttcgtacg ctagctaaaa ctaaaactaa   1260
cataagttgg ataccttgag gatcagattc tgaaataggt cgccagattg gcagaaaccg   1320
cgcgcacgca aatcaaatac aacgtgcgca ggtagcgccc ggccgaccgg tgtccccgcg   1380
cccgctggtc gatggagagg cctagggcct agcggatgcg gtccatcccg attcccatca   1440
gcactgcctg ccaacgcggc agcggccgcg ccgaccgcga cccgcagcga gcacgggcgg   1500
cccagggagg ccacgtccca cccacctctc ccatggccgt ttccccgggg ggcgacgcgt   1560
tcgcccacca gcagccggcc gaccggtgtt ggccccaccc caagcaccca cctctggcgt   1620
ggcaacgtgc cgcaattcgg ccacccaggc acggtgggca aaggatggga caggcatggg   1680
cggccgagca acctcgctgt ctcgggcacg cacgcactct cccgccagct ttcgcgctgc   1740
gtccagcccc ggccgctata tggaccacgc cacgcccctg actgacgccc gccagccgat   1800
tcccccggtg ggctgggctg gctggggcgc gcacacgcgg cgcccctcgc ctgccgcggg   1860
ctgcggcgcc ccacgccacg cggcgttcgg cccttgcgcg cgacctgcgc cagccaggcg   1920
ggagatagag agagagagcc gctgagctga ggacgtccaa ccgccagtgg ctctgtctga   1980
cttgactcaa gatgccgtgg gcgtcgccgt tgaattgcat ggccaggaac atagagacgg   2040
gtttcgcttt gcttcggttt ggggctcggc tcgttcgctg gctgctacag ttgatttgag   2100
gctccacccc tccctttttta gctactcact ctgtcatgac tcatgactca gcactcggca   2160
aatatctcaa ctttgcattg catcctacta cagcaccgga gagcagaatc aggctactcc   2220
gtcagccgcg tcagggtgtg gtaatagtag tacatcatac acacctctcc gagactccga   2280
ccactcccctt cccatgccta tataaacaga ggccacctcc ttcgtccctc ccgcccccat   2340
caagattccg acccaaatcc ctctccgagc tcgaccaaaa accaccctcc cagtacgtac   2400
attcccacca cctcccagtg cagcgccagt ctgtaaccca taaccataac catacc       2456
```

<210> SEQ ID NO 13
<211> LENGTH: 2500
<212> TYPE: DNA
<213> ORGANISM: Zea mays

<400> SEQUENCE: 13

```
tctcctttc  tttgtttcac  atctttcgt  atcacgtcat  tgaatcaatc  gcgcgcttcg    60
atcctccgtt  ttcgctcgag  ttgctgtcga  aatctaatgc  cgatggcgag  aggctggaac   120
gggagtcggt  ccacgttgca  atctgaccca  cacggtgtag  atggctactg  actgtgtgac   180
atgtaataaa  agaacgaaag  cgcacacgcg  cgcacaaaaa  aaaaactgca  gctagcacgt   240
actggtgcaa  tgcaacgaac  gagcctcgat  cgatcggaca  tgaacatggt  catggtgttg   300
gcgactttga  tcctttgagt  agatgatctg  ctgtacgtac  gtcaagttat  cgagtagatc   360
aattggtcct  tatcatacca  acattcatac  attgggttag  caatctgttt  agcgccggcc   420
actatggagg  cgcgcggcga  tcatcttgac  atgtgcatgg  agggatttat  ctaggtaaca   480
acacatcaac  ttggtgctcc  caagataggg  aaggagctga  acatgccata  tgatataatt   540
gatcttcgtg  aggcgaatga  taaataacat  catgatgtat  tggaatagga  gcaaaggtgg   600
tgggtcataa  ggacgacatc  atgatgtatt  ggaacagaaa  cggaggtagg  tcatatttga   660
catggtggat  ggaaatgagg  aagaagtatg  datggcaatg  ggtcaggttt  tagacgggtg   720
gagcaaaaac  ccgcccatga  tcgcacctgt  gatgtctacc  taaaaaacca  cccgcaatag   780
cacccacgag  caccattcta  gacccgcact  caaacacgtc  ggatttccgg  tcaccagcgg   840
gtttctaccc  gataaacaat  tttaaacaat  aattcggcta  taaacaatta  agtaccggta   900
ataattgagt  tatatctata  gattttttaa  gccttgttac  gttgagcagc  cacaaaacat   960
ttcatgaatg  attagctaag  ttacttattc  aaaacatttt  tctattgtat  cttaatcatt  1020
tttgcacata  ataagaatg   aactaaattt  cggatcggtg  tggatcaccc  acgggttaaa  1080
atagaaacat  gtactcacgc  cttcaaaact  ctgggtcaag  tgcgggacac  cgatgggtta  1140
aaataaaaac  tcgtatccac  atccacgaaa  cttcatatta  ggtgcggggt  actcgcgatt  1200
caaaaccttc  acacttaccc  gcacccgtcg  gtgctgcaag  ttaaattgtc  attcctagga  1260
agaaggaatg  gaagttatgg  tagagatatt  ctaaaaatgt  ttccttagct  ttggtatcat  1320
gttaattgaa  ttgctaaaag  actatcgatc  gaccctacga  gttaaaacct  attctttata  1380
tagatcactg  attttatctc  ctatttcaaa  ggggagagc   tcctgaaatc  aagatgttgc  1440
taaaggaaaa  cataatatta  ttctatcata  ttttatctcc  tatttcaaac  aatatttttcc 1500
actgccatat  acatacaggc  ccgtgccaga  ggacgtgcgg  gtgcgggctg  tgcaccggaa  1560
cagggcccct  aaatatttag  ggcctccaaa  tgtgtaaatt  tacagtacat  ttatataata  1620
gtctatttt   gtactatata  aaaacacaag  ttgttttggt  tccaccttgt  cttcacatta  1680
aaattgaaaa  aatgttaata  taatgtcgga  tcactttgcc  aattagtatg  aatgcaaatag 1740
agataatagt  tagctgttaa  aattagctaa  agacattcaa  acaatatagc  taatagctcg  1800
gctattaacc  tcttttagta  aattaactaa  tggttagcta  gctatttgtt  agctagcaat  1860
tttcagtcaa  ttaattatta  gctttaatgc  attcaaacat  ctctaattct  ttattaatat  1920
gtctgtacgt  atgcttttat  tccatgacgt  gaggaatgag  tttagccata  acccgcatac  1980
ctgcaatttt  acgatgtttt  gttcaccgat  atctaacgtc  ctcgactagt  aaagaggtct  2040
tattttaaaa  tctgtacagg  gcctcggatt  ttgtcggcac  ggccctgtat  acataaaatc  2100
tgttagacat  ttagacacag  ccttagagac  ttaactatgt  tcaagaagac  gttgtttcat  2160
gaaaagaat   aatgttgtac  catctagaca  taatgttaac  aatagcaaac  attctcttgt  2220
caaactaagt  tatggttcat  cttgcgtgta  actaacttct  gtttctacat  tgtagatcag  2280
acgtacggcc  agtgatctcg  gccagcgatg  cttgatcgta  cggccagaat  taccacacca  2340
```

```
cgctgcggtg aggactgagg acttccccgc gcgccactgc tccgcccgcg tccgcgtcta   2400
tacaaaggct gtcgcgctcg gcactcttgc tgtcgcgctc tgtgcacaga cgaccttctt   2460
cccatccctt ccctctgcta gtctgcttcg ttcctcggcc                         2500
```

<210> SEQ ID NO 14
<211> LENGTH: 2472
<212> TYPE: DNA
<213> ORGANISM: Zea mays

<400> SEQUENCE: 14

```
acccattttc gactactgtg aacctcttgc ttcccgtcat ctaatcttag aaacatttgt     60 accacccta gagtcaatct ctcactctat ttcactcatt tatatgatga gttatacaac    120
taggactctt aaattggtat ggattatcac aaaaaaatga tctatgacta tgacaaccta   180
ttagaaaacc tgtggcacat aaaagagatt agcctagaca catgtcttaa caaccctcct   240
tagtcacaac ttcctaagtt gatactgtac tcaaagtttt atagctgata tgcactgaaa   300
catctttaat gagaccatcg acaatctaac cttcagtgaa tacatataag atcaaccta    360 agaagcttat ttataactct ttatatatct cacaaaatgg ctatatatca acttatatat   420
gtttagttcc aggaaggaaa gcttccatat gtttcttcta atatggaaat ttgccacctt   480
caaagatgag aggaggtcca tttacactgg acatggtaaa ccaaaatagt taaactaaac   540
aaatgagcac aaggatttca tacaatcgat ttatgtaaag aatagatcat gacgacccat   600
ataatcaaca gagtctttga gcaataattc aatcaacacg cggttgttaa gaatgaatag   660
caaagtaata gtatatatac gtactttgca tatatatgat tttcttctaa ttgggtacac   720
tctttttttt ctttattttc tatcagccac aagctaacag cattggaaaa ctcagctgca   780
tgcgattaca gagaccgaaa ttttttcatt ttctagaaaa acatatcgat cttaactcaa   840
ttaacacaac cattacacaa tggacatttt atgaaagggt tagatataac ttggcgaaag   900
tcatgaagcg agccatgtgg cctgacagcc tatatacaga ctcaccacta acagtatcta   960
acaaaacata tacatatgac ctcacaactt atatatcaat cggttgctca cggcaactaa  1020
ggctctattt aatttaatac tcttcgttct aaaaatataa ttgttttaga ctaaacatat  1080
attcattaat taaactacga agatgttgc ctataatagc tcatatataa aggtctgttt   1140
ggttatatta tgactgtaaa aaaaattgtt gtggggtgtg agttattaaa aagataaaaa  1200
ccgtttgata caaaccacta aaagcagtta aaagttcttc gatatatgtt gtcacaccca  1260
tctgaaaagc cactaaaagc aggtctagag gtgttttag ttttgcagtg cgagaaagtc   1320
ggcttttaga agaaaaaaat gtttcctgga tccagcccct tggtttggtt tttggctttt  1380
agagtgcaaa agctaaacca aacacaccct aatataagct actatagatg tccaacaagt  1440
ctgaagctcg aaaggccgac cccaagcacg ttttttttg gctcggtacg agcacgcccc    1500
cgtctgttta aaacggtcc aagccgaccc gatacgaata tgtatgctag gtccggacag    1560
agaattaagc acgtcgtgct ggcccgacac ggcctatttt ttactgagct gtgcttttcg  1620
acctgttaag cccgcttttt tcgtgcttct gggccggccc gatccgttta agcccgtagc  1680
gtgttagacc cgttcaggga ataagcttg tgggtctacc aaacctggcc cggttttcta    1740
acgtgcctga cgggcctggc ctgaactgag tcgtgtttca ccggaccagg ccagacgccg  1800
gtttgaacat cactacaagc aactctaaaa gatgtttgat gtgtaactat tagtcagcta  1860
acaattatta gcaggttttt gttatttctc catatctatt agctgcaatt atctgacctc  1920
gtcgaactag taggatagtt attattatct atgagtctag ctaacgtgtt tggattgaag  1980
```

| | |
|---|---|
| acagataatt attgccagat aaccaatatc tattggagat ccaaaccggg cctaaccaac | 2040 |
| acacaaaagc aacgagagag taaagctgtc tcttcggcaa cgccaacttg catacaaaag | 2100 |
| attgaggtcc caatcctaag gatcaattat tgcaaattta actggagtca tggaatttct | 2160 |
| tggaggaaac cacagattgt tggcaacagc ggcaagcaaa ggcttacggc cctgatctcg | 2220 |
| gccagtgatg cttgatcaga cggctagaat taccagatcg cgctgtgcta ggtcgctgac | 2280 |
| ggtctgtcta gtcatccacc gactccccgc ccgcgccacc actgctcggc gtgtctactc | 2340 |
| actcggtcac tcctatataa gacgctcgct cgcggcacta ctgctctcgc gctcgcgctc | 2400 |
| tgtgcacaga cgagagacga ccttcccttc ccgttcctct gtttttatct ctgctccatt | 2460 |
| cctcgatcgg cc | 2472 |

<210> SEQ ID NO 15
<211> LENGTH: 1554
<212> TYPE: DNA
<213> ORGANISM: Arabidopsis thaliana

<400> SEQUENCE: 15

| | |
|---|---|
| atgtctccgg aagcttacgt tctgttcttt aacagtttta acctcgtaac cttcgaagcc | 60 |
| tttgcttcag tctcacttat catagccaca gttgctttct tgctctcacc aggtgggctc | 120 |
| gcatgggcct ggaccgggtc atccaagagt cgggtttcga ttccaggacc atctggttct | 180 |
| cttccgtct ctccggctc caatccccac cgtgttctcg ccgctcttgc taaacgcttc | 240 |
| aaggcctctc cgttgatggc gttctcagtt gggttttcgc gtttcgttat ctctagtgaa | 300 |
| ccggagacgg ctaaagagat tttgagcagc tctgcttttg ctgaccggcc ggttaaggag | 360 |
| tcagcttacg agcttttgtt tcaccgtgcc atgggattcg caccgtatgg tgagtattgg | 420 |
| aggaatctga ggagaatctc ctccactcat cttttcagtc aagaagaat cgcgagtttt | 480 |
| gagggtgtta gagttggcat cggtatgaag atggtcaaga agattaaaag ccttgttacg | 540 |
| tctgatgctt gtggtgaagt tgaagtgaaa aagatcgttc actttggttc tttgaataat | 600 |
| gtaatgacga cagtgtttgg tgaaagctac gattttgatg aagttaatgg aaaagggtgt | 660 |
| tttttggaga ggctggtgag tgaaggctac gagttgcttg ggattttaa ctggagtgat | 720 |
| cacttttggt ttcttcgttg gtttgacttc caaggagtga ggaagaggtg tagagctttg | 780 |
| gtctctgaag tcaacacttt tgtcggcgga ataattgaga acacaagat gaagaagggt | 840 |
| aataatctca atggagagga aaatgacttc gttgatgtct tgcttggctt gcaaaaggat | 900 |
| gaaaagttgt ctgattctga catgattgct gttctttggg aaatgatatt tagagggaca | 960 |
| gatacagttg cgattctagt ggaatgggtg cttgcaagaa tggttttgca tcaagacatc | 1020 |
| caagataaac tctacagaga gatagcttct gctacaagta acaatattag atccttgtct | 1080 |
| gattccgaca tcccaaaact gccgtacctt caagctattg tcaaagaaac cctaaggctc | 1140 |
| cacccccctg gtccacttct ctcttgggct cgtctcgcta ccatgacgt ccacgtaggt | 1200 |
| cctaaccttg tccctgctgg aaccatagct atggtcaaca tgtggtccat cacacacaac | 1260 |
| gctaaaatct ggaccgaccc tgaagcgttt atgcctgaaa ggttcattag tgaggatgtg | 1320 |
| agcatcatgg gctcggatct tagattggct ccattcggat ccggtcgtcg ggtttgtccc | 1380 |
| ggtaaagcaa tgggtctagc tactgttcat ctctggattg gtcaactaat tcagaatttt | 1440 |
| gaatgggtga agggttcttg tgatgttgag ctcgctgagg ttctgaagct gtctatggag | 1500 |
| atgaagaatc cgttgaagtg caaggctgtt ccaaggaatg ttggtttcgc ttga | 1554 |

<210> SEQ ID NO 16
<211> LENGTH: 1647
<212> TYPE: DNA
<213> ORGANISM: Zea mays

<400> SEQUENCE: 16

| | |
|---|---|
| atggcgatgg cctccgcggc ttgctcatgc acggacggca cgtggtgggt gtacgcgctc | 60 |
| ccggcgctgc tcggctccga caccctgtgc gcccacccgg ccctcctggc tggcctgatc | 120 |
| tttctggcca ccgtctcggt ggctctgctg gcgtgggcca cgtcgccggg cggtccggcg | 180 |
| tggacgaacg gccgcggccg cctcggcgtc actcctatcg tgggaccccg tggtctgccc | 240 |
| gtgttcggca gcatcttcgc gctgtcccgc gggctgccgc accgcgccct cgccgagatg | 300 |
| gcccgcgccg cagggccccg ggccaaggag ctcatggcgt tctccgtcgg tgacacgccc | 360 |
| gcggtcgtgt cgtcctgccc ggccacggca cgtgaggtgc tcgcgcaccc gtcattcgcc | 420 |
| gaccgccctg tgaagcggtc ggcccgggag ctcatgttcg cgcgtgccat cgggttcgcg | 480 |
| cccaacggcg agtactggcg ccgcctccgc cgcgtcgcgt ccacgcacct attctccccg | 540 |
| cgccgggtcg cctcgcacga ccgggacgc caaggtgacg cggaggccat gctccgctcc | 600 |
| atcgccgccg aacagtcggc ctctggcgcc gtcgccctcc gcccgcacct ccaggccgcc | 660 |
| gctctcaaca acatcatggg cagcgtcttc ggcacgcggt acgacgtcac atcaggcgcc | 720 |
| ggcgccgcg aggccgagca tctcaagagc atggtgcgcg aggggttcga gctcctcggc | 780 |
| gccttcaact ggtccgacca cctcccctgg ctcgcccacc tgtacgaccc aagcaacgtc | 840 |
| acccgccggt gcgccgcgct cgtgccgcgc gtccagacct tcgtccgtgg cgtcatcgac | 900 |
| gagcaccggc gccgccgcca aaactccgcc gccctcaacg acaatgctga cttcgtcgac | 960 |
| gtgctcctct ccctcgaggg tgacgagaag ctcggcgacg acgacatggt cgccatcctc | 1020 |
| tgggagatgg tcttccgcgg tacggacacg acggcgcttc tgaccgagtg gtgcatggcg | 1080 |
| gagctggtgc gccacccggc ggtgcaggcg agggtgcgcg ccgaggtcga cgcggctgtc | 1140 |
| ggtgccggag gttgccccac cgacgccgac gtggcgcgca tgccgtacct gcaggcggtt | 1200 |
| gtgaaggaga cgctgcgcgc ccacccgcct ggccgctgc tgagctgggc tcgcctcgcc | 1260 |
| accgccgacg tgccactctg caacggcatg gtggtcccgg ctggcaccac ggcgatggtg | 1320 |
| aatatgtggg cctaacccca cgatgccgcc gtgtgggccg acccggacgc gttcgcgccg | 1380 |
| gagcggttcc tgccctccga gggcggcgcc gacgtggacg tccgcggcgt cgacctccgc | 1440 |
| ctggccccgt tcggcgccgg cgtcgcgtc tgccccggca agaacctggg cctcaccacc | 1500 |
| gtgggcctct gggttgcccg cctcgtgcac gccttccagt gggccctgcc tgacggcgcg | 1560 |
| gcggccgttt gcctcgacga ggtcctcaag ctctccctgg agatgaagac gccgctcgtc | 1620 |
| gccgcagcca tcccccgcac cgcctga | 1647 |

<210> SEQ ID NO 17
<211> LENGTH: 1458
<212> TYPE: DNA
<213> ORGANISM: Zea mays

<400> SEQUENCE: 17

| | |
|---|---|
| atggcgatgg cctccgcggc ttgctcatgc acggacggca cgtggtgggt gtacgcgctc | 60 |
| ccggcgctgc tcggctccga caccctgtgc gcccacccgg ccctcctggc tggcctgatc | 120 |
| tttctggcca ccgtctcggt ggctctgctg gcgtgggcca cgtcgccggg cggtccggcg | 180 |
| tggacgaacg gccgcggccg cctcggcgtc actcctatcg tgggaccccg tggtctgccc | 240 |

```
gtgttcggca gcatcttcgc gctgtcccgc gggctgccgc accgcgccct cgccgagatg      300
gcccgcgccg cagggccccg ggccaaggag ctcatgbcgt tctccgtcgg tgacacgccc      360
gcggtcgtgt cgtcctgccc ggccacggca cgtgaggtgc tcgcgcaccc gtcattcgcc      420
gaccgccctg tgaagcggtc ggcccgggag ctcatgttcg cgcgtgccat cgggttcgcg      480
cccaacggcg agtactggcg ccgcctccgc cgcgtcgcgt ccacgcacct attctccccg      540
cgccgggtcg cctcgcacga gccgggacgc caaggtgacg cggaggccat gctccgctcc      600
atcgccgccg aacagtcggc ctctggcgcc gtcgccctcc gcccgcacct ccaggccgcc      660
gctctcaaca acatcatggg cagcgtcttc ggcacgcgt acgacgtcac atcaggcgcc      720
ggcgccgcgg aggccgagca tctcaagagc atggtgcgcg aggggttcga gctcctcggc      780
gccttcaact ggtccgacca cctccctgg ctcgcccacc tgtacgaccc aagcaacgtc      840
acccgccggt gcgccgcgct cgtgccgcgc gtccagacct tcgtccgtgg cgtcatcgac      900
gagcaccggc gccgccgcca aaactccgcc gccctcaacg acaatgctga cttcgtcgac      960
gtgctcctct ccctcgaggg tgacgagaag ctcggcgacg acgacatggt cgccatcctc     1020
tgggtaaagt tcaaatcgat cgcttttccta gcttgtttaa ctgcgcatac ttctcagttc     1080
tcaactgcgc atacctgtcg gttctacagt tttgtgtcgg gctgtcggtt gttcccggaa     1140
gggaaaaaaa agaacaaagt gtgggcccaa ccagacgcgt tcgcaccgga gcggttcctg     1200
ccctccgaag ggcgggcgcc gacgaggacg tcccgcggcg tcgacctccg cctggccccg     1260
ttcggcgccg ggcgtcgcgt ctgccccggc aagaacctgg gcctcaccac cgtgggcctc     1320
tgggttgccc gcctcgtgca cgccttccag tgggccctgc ctgacggcgc ggcggccgtt     1380
tgcctcgacg aggtcctcaa gctctccctg gagatgaaga cgccgctcgt cgccgcagcc     1440 atccccgca ccgcctga                                                     1458

<210> SEQ ID NO 18
<211> LENGTH: 1668
<212> TYPE: DNA
<213> ORGANISM: Oryza sativa

<400> SEQUENCE: 18
atggcaatgg ccaccgccac cgcctcctcc tgcgtcgacg ccacgtggtg ggcgtacgcc       60
ctcccggcgc tcctcggcgc cgacaccctc tgcgcccacc cggcgctgct cgccggcgcc      120
gtcctcctgg ccttcgccac cgccgcggtg ctcgcctggg ccgcgtcccc ggcgggccg       180 gcgtgggcgc acggccgcgg ccgcctcggc gcgacgccca tcgaggggcc ccgggggctc      240
cccgtgttcg gcagcatctt cgcgctctcc cggggcctcc cgcaccgcgc gctcgacgcg      300
atgtcgcgcg acgcggcggc gccacggcg agggagctca tggcgttctc cgtcggggag      360
acgccggcgg tggtgtcgtc gtgcccggcg acggcgaggg aggtgctcgc gcacccgtcg      420
ttcgccgacc gcccgctgaa gcgctcggcg cgggagctgc tgttcgcgcg cgccatcggg      480
ttcgccccca gcggcgagta ctggcgcctc ctccgccgca tcgcctccac ccacctcttc      540
tcccctcgcc gcgtcgccgc gcacgagccg gggcgccagg ccgacgccac ggcgatgctg      600
tccgccatgg ccgccgagca gtccgccacc ggcgccgtcg tgctccgccc ccacctccag      660
gccgccgcgc tcaacaacat catgggcagc gtgttcggcc ggcgctacga cgtctcctcc      720
tcctccggcg ccgccgccga cgaggccgag cagctcaaga gcatggtgcg cgaggggttc      780
gagctcctcg gcgcgttcaa ctggtccgac cacctcccat ggctcgccca cctctacgac      840
```

```
cccaaccacg tcgcccgccg ctgcgccgcg ctcgtccccc gcgtccaggc gttcgtccgc    900
ggcgtcatcc gcgaccaccg cctccgccgc gactcctcct ccaccgccgc cgacaatgcc    960
gacttcgtcg acgtcctcct ctccctcgag gcccacgaga acctcgccga ggacgacatg   1020
gtcgccgtcc tctgggagat gatatttcgt gggacggaca cgacggcgtt ggtgacggag   1080
tggtgcatgg cggaggtggt gaggaacccg gcggtgcagg cgaggctgag gcggaggtg    1140
gacgcggcgg tgggcggcga cgggtgtccc agcgacggcg acgtggcgcg gatgccgtac   1200
ctgcaggcgg tggtgaagga gacgctgagg gcgcacccgc cggggccgct gctgagctgg   1260
gcgcggctgg ccaccgccga cgtgggctc gccaacggca tggtggtgcc ggcgggcacg    1320
acggcgatgg tgaacatgtg ggccatcacc cacgacggcg aggtgtgggc cgacccggag   1380
gcgttcgcgc cggagcggtt catcccgtcg gagggcggcg ccgacgtcga cgtccgcgac   1440
ggcgacctcc gcctggcgcc gttcggcgcc gggcgccgcg tctgccccgg caagaacctc   1500
ggcctcgcca ccgtctccct ctgggtcgcc cgcctcgtcc acgccttcga ctggttcctc   1560
cccgacggct cgccgccggt gtccctcgac gaggtcctca agctctcccct cgagatgaag   1620
acccctctcg ccgccgccgc cacccccccgc cgccgccgcg ccgcctga              1668

<210> SEQ ID NO 19
<211> LENGTH: 1611
<212> TYPE: DNA
<213> ORGANISM: Arabidopsis thaliana

<400> SEQUENCE: 19
atggagttga tgaatttggc ttcaaaagaa caagctatt ggatgattgc actgcctgcc      60
ggttttggat cccaaaaacct acatgatgtt tccaccctag ctatctatt ccttgccgtc    120
gttttctct ctatagtcac gtgggctctc gccggaggcg tggtgtcgc ttggaagaac      180
ggccgtaacc ggttgggtcg tgtcgcgatc cctggtcctc gtggcatacc agtattcggc    240
agtcttttca ctctcagccg aggcttggct catcggacgt tagcagccat ggcttggagc    300
cgagccaaca ctgagattat ggcttttagc cttggttcaa cgccggttat cgtggcttct    360
gaaccaaaca tagctcgtga gattctgatg tcgcctcact tcgcggaccg gccggttaag    420
cagtctgcta agagcctcat gttcagccga gccataggtt tcgccccaaa cgggacttac    480
tggcgcatgt taagaaggat cgcatcgact cacctatttg ctcctcggcg tatcttagca    540
cacgaagctg gcgccagct agactgcgct gaaatggtga agctgtgtc agtggagcaa      600
aacgcgctg atcagtcgt tttaaggaaa cacttacaac tagccgcctt gaacaacatc      660
atgggaagtg tttttgggag aagatacgat cctctggctc agaaagagga tcttgatgag    720
cttacatcaa tggttaggga agggttcgag cttttgggtg cttttaattg gtctgattat    780
cttccatggc tcggttattt ctacgactca attcgtttaa accaacgttg ctcagatctc    840
gtccctcgaa ttagaacccct cgtcaagaaa atcatcgacg aacatcgagt tagtaactct    900
gagaagaaaa gagacattgg agattttgtt gatgtcttat tgtctttaga cggtgatgag    960
aaacttcaag aagatgacat gatcgccgtt ttatgggaga tgattttttcg agggacagat   1020
acaacggcgt tattaacgga gtggaccatg gccgagctag tactgaaccc taacgtgcaa   1080
accaagttac gagacgagat tttaactgct gtgggcgacg gcgccgacgg agacgtggca   1140
gatgctgacc tggcaaaaact cccgtaccta aacgcagtgg tgaaggaaac tctaaggctg   1200
catcctcctg gaccactgct ttcatgggct cgtctttcca cgtcagacgt ccagctcagc   1260
aatggcatgg tgattccaaa gggaactaca gcgatggtca acatgtgggc tataacccac   1320
```

-continued

```
gaccagactg tatggtccga cccgctaaag tttgacccgg agagattcac tgggaatgct    1380
gacatggata ttcgtggtgg ggatctaagg cttgcaccgt ttggagccgg taggagagtg    1440
tgtccgggga agaacatggg gctagctact gtgactcggt gggtggctga gttggtacga    1500
cggttcgagt ggggtcagga tcagaccgag ccagttgatc ttggtgaggt cttgaagctt    1560
tcttgtgaga tggagcatcc gttacgtgcc gttgtaacgg aaatatttta a             1611

<210> SEQ ID NO 20
<211> LENGTH: 1650
<212> TYPE: DNA
<213> ORGANISM: Physcomitrella patens

<400> SEQUENCE: 20
atggattcaa ccacgtgtga agtaggagga ttgtggctgt ttgctttgcc tatgctcgcc      60
aaacaaggga gatcttcttt ggaagaggct ttgggatgca caaacttcag cagcattctt     120
tgtattgtgg gtgtgataag tgcttgtgcc ctgttggtgt gctgggcttc gcctggcggc     180
tcctcgtggg gccgcttgag atgtgtgaaa accatcccag gccccgaggg gtttcctgtc     240
atcggttcac tgttggagat gggaggactg gcccacaggc gccttgctca acttgctgta     300
acgtacaaag ctacagcatt gatggcgttg agcttaggag aaacgcgtgt ggtgattgct     360
agccaaccgg ataccgcgcg cgagattcta catagtacgg cattcgcaga tcgaccctg     420 aagcagtcag cccagcagct cttgttcggg cgcgctattg ggtttgctcc ttacggaggt     480
tattggcgta acttaagacg aattgcggct aatcatttgt tcgctcccaa gcggattgca     540
gctcatggga agacgcgtct cgatgagtta gccctcatgc tcaatgccat ccagagagaa     600
gttgagacta caggtcacgt gctcattcga ccgcacttgc agagagcctc tctcaacaat     660
atcatgggca gtgtgtttgg gcgtaggtat gacttcgtct tgggttctga ggaggcgaat     720
gagttagggg cccttgtaaa agaaggattt gaactactgg gtgcgttcaa tttggccgat     780
cacctgccag ttttgaagtg tctcgacgcc cagaatattc tccagaggtg cgcggctctt     840
gttcctcgag tcacagcgtt tgtgaagaag atcattgatg aacaccggca gaggagggat     900
gtacgtgcta ccactggaga gagctatgag gaggacttcg tggatgtctt gctcggtctc     960
accggggagg agaagctgtc cgaggaagac atgatcgccg tgctttggga tgatgcttc    1020 agagggactg atactactgc cattctcacg gagtggatca tggcggaaat ggtgctgaac    1080
cctgaaattc agtgcaatgt ccaacgcgag ctcgactctg ctttcagaaa gaagaatatc    1140
accgatttca cgtcattgga aagcgagttg tccaggttgc cctacctcca ggccgtgatt    1200
aaggaaaccc tccgacttca ccctcctggt ccgctcctct catgggccag actctccacc    1260
caggatgttt gtatcgctgg gcatctaatc cctaaacaca ccaccgcaat ggtgaacatg    1320
tgggcaatta cgcacgaccc gaagttgtgg gctaacccga acgaattcat tccagagaga    1380
tttcttcctt cacatggcgg tcaggacgtt gacgttcgtg gaaacgacct acgcctggcg    1440
cctttcggcg ctggccgacg cgtctgtccg ggacgcgcgc ttggattggc cacagtgcaa    1500
ctttgggtag cacagttatt gtataacttc aaatggaccg cagttccagg gtgcgatgtt    1560
gacctcaccg agattttgaa gttgtcatcc gagatggtga agccattgca atctgtcgct    1620
actcgccgcc tggtagatcc gtcaagctag                                    1650

<210> SEQ ID NO 21
<211> LENGTH: 1653
<212> TYPE: DNA
```

-continued

<213> ORGANISM: Physcomitrella patens

<400> SEQUENCE: 21

```
atggattcag ctcccactca agtcggaggg tggtggtggt ttgctgtgcc cttgctggcc      60
aagcagggaa gatcctcgct ggaggaggcg gcgggatata caaacctcaa cgggctggtg     120
attatgctcg tattgggtgt gataagtgct tgtgctatat tcgtttgttg gatttctccc     180
ggaggttcgt catggggacg tttgagaggt aagagaacca tccccgggcc tcgagggttt     240
cccatcatcg gttccctgtt ggatatgggt ggattggccc acaggcgtct cgctcagctt     300
gctgtagcct acaaagctat gccgctgatg gctttaagcc taggagagac ccgtgtggtg     360
attgctagtc aacccgatac tgcccgtgag attttgcata gtgcgggttt cgccgaccgg     420
ccgctgaagc agtccgctga tcagctcatg ttctcacgcg ccattgggtt tgcttctcat     480
gggaaatact ggcgaagttt aagacgaatt gcagccaacc atttgttttc gcccaagagg     540
attgctgagc acgaggattc gcgtgttgct gaatctgagt tcatgctaca atctattgag     600
aatgaccttc tcgtattggg cagcgtccag attcgtggtc acctgcaaag agcgtccctg     660
aacaatatca tgcgtagtgt gtttgggcgg cggtatgact tcgtcactgg atctgaggag     720
gcaacccagt tgagggccat ggtggatgaa ggatttgatt tgcttggtgc tttcaattgg     780
gctgatcact tgccagccct gaagtttctg gacgcacaga agatacatca aagatgcgct     840
gatctcgttc ccagagtcag aacatttgtt cagaaaatca ttgatgaaca ccgcaatgaa     900
aataactctc gtgtgggcgc tgacgagagg cgtgaaactg attttgtaga cgtcttgctc     960
tccttgaaag gtgatgagca gcttgccgac gaggatatga tcgctgtgct ttgggagatg    1020
atatttagag gaactgatac caccgctatc ctgaccgagt ggattatggc ggaaatggtg    1080
ctgcaccccg aaattcagcg caaggttcaa ttcgagctgg actccgtttt tcccactggt    1140
atctgcaact gcgcatcttt tgaaaatatg cttccagat  taccctacct aaaggccgtg    1200
gtcaaagaaa ctctccgtct gcatcctccc ggtcccctcc tctcatgggc aaggctatca    1260
gttcaagatg tttgcgtagc tggacacaca attcctgcgg gcacgacagc aatggtaaac    1320
atgtgggcaa tcacccacga tcctgaagtg tgggctaatc cgagtgtatt ctctcccgag    1380
agatttctgc cttctcatgg tggccaggat gtggatgtcc gtggcaacga tcttcgcctg    1440
gctcctttcg gggctggccg tcgtgtctgt ccagggcgtg cactcggatt agccactgtg    1500
cacctgtggg tggcgcagct gttgcacaac ttcgaatgga ccccggcacc agtgtgcgaa    1560
gtggaccta ccgaggtatt gaagctgtct tcagagatgg tgaacccact gcagtccgtt    1620
gctactagtc gccgagtatc cacatcgggc taa                                 1653
```

MEANS AND METHODS FOR YIELD PERFORMANCE IN PLANTS

CROSS-REFERENCE TO RELATED APPLICATIONS

This application is a national phase entry under 35 U.S.C. § 371 of International Patent Application PCT/EP2014/061438, filed Jun. 3, 2014, designating the United States of America and published in English as International Patent Publication WO 2014/195287 A1 on Dec. 11, 2014, which claims the benefit under Article 8 of the Patent Cooperation Treaty and under 35 U.S.C. §119(e) to United Kingdom Patent Application Serial No. 1309866.0, filed Jun. 13, 2013.

TECHNICAL FIELD

This disclosure relates to the field of plant molecular biology, more particularly to the field of agriculture, and even more particularly to the field of improving the yield of plants. This disclosure provides chimeric genes and constructs that can be used to enhance the yield in plants and crops.

BACKGROUND

Since the beginning of agriculture and horticulture, there was a need for improving plant traits in crop cultivation. Breeding strategies foster crop properties to withstand biotic and abiotic stresses, to improve nutrient use efficiency and to alter other intrinsic crop-specific parameters, i.e., increasing yield by applying technical advances. In the coming decades, a crucial challenge for humanity will be meeting future food demands without further undermining the integrity of the Earth's environmental systems. Agricultural systems are already major forces of global environmental degradation, but population growth and increasing consumption of calorie- and meat-intensive diets are expected to roughly double human food demand by 2050. Responding to these pressures, there is increasing focus on "sustainable intensification" as a means of increasing yields on underperforming landscapes while simultaneously decreasing the environmental impacts of agricultural systems. Conventional means for crop and horticultural improvements today utilize selective breeding techniques to identify plants with desirable characteristics. Advances in molecular biology have allowed modification of the germplasm of plants in a specific way. For example, the modification of a single gene resulted in several cases in a significant increase in yield or yield-related traits.

Cytochrome P450 monooxygenases are a superfamily of heme-dependent enzymes that are involved in the biosynthesis and detoxification of a wide variety of molecules. A number of cytochrome P450-mediated reactions give rise to products necessary for the control of cell expansion in plants. The CYP78A5 gene is a cytochrome P450 monooxygenase (S. C. Zondlo and V. F. Irish (1999), *The Plant Journal* 19(3), 259-268) that is strongly expressed in the peripheral regions of the vegetative and reproductive shoot apical meristems. The overexpression of CYP78A5 affects multiple cell types, causing twisting and kinking of the stem and defects in floral development. In addition, the constitutive overexpression of CYP78A5 leads to smaller leaves in transformed plants.

SUMMARY OF THE DISCLOSURE

In this disclosure, it is surprisingly shown that a chimeric gene construct wherein the corn CYP78A5 is controlled by a corn GA2 oxidase promoter leads to more than a 30% increase in leaf size in corn. This novel trait can be used for increasing the yield in plants, in particular, crops such as, for example, cereals.

BRIEF DESCRIPTION OF THE DRAWINGS

FIG. 1: Sequence of GA2 oxidase promoter derived from GRMZM2G031724; attB1 and attB2 sites are underlined (SEQ ID NO:1).

FIG. 2: Sequence of KLUH gene (GRMZM2G167986); attached attB1 and attB2 sites are underlined (SEQ ID NO:2).

FIG. 5: Sequence of the resulting chimeric gene "GA2 oxidase promoter (GRMZM2G031724) operably linked to the KLUH gene (GRMZM2G167986)" that was incorporated in the plant expression vector (SEQ ID NO:3).

FIG. 11A, seedlings at 30 days after sowing; the arrows indicate leaf 4. FIG. 11B, fully grown plants at 115 days. FIG. 11C, growth rate or LER (Y-axis: mm/h and X-axis days of leaf 4 growth).

DETAILED DESCRIPTION

Figure 3:
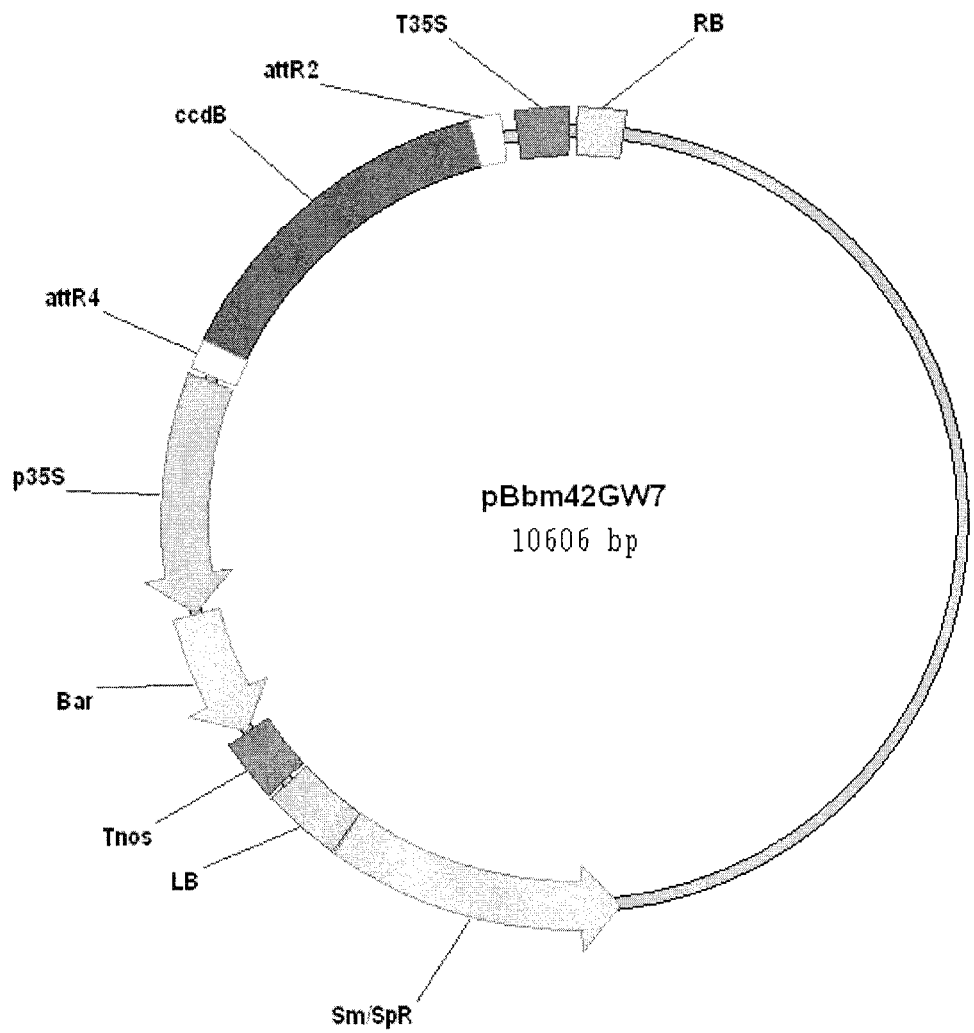
FIG. 3: Structure of pBb42GW7 vector.

The growing maize leaf provides an excellent model system to study the role of cell division and cell expansion in organ size control since these two processes occur spatially separated within the growth zone. In a maize seedling, the fourth leaf is growing at a maximum rate just after emergence from the sheath of surrounding older leaves. Its growth zone is located at the leaf base, which means the leaf has to be dissected from the sheath in order to access the growth zone. In this way, the growth zone of the fourth leaf can easily be sampled with a high spatial resolution due to the relatively large size of the growing maize leaf.

In this disclosure, it has been shown that numerous transcripts show a differential expression within the different samples that make up one zone, indicating the distinctions within the growth zone. Similarly, growth-regulating hormones, auxins and cytokinins are higher in the basal part of the division zone compared to the more distal part (Nelissen et al., 2012, *Curr. Biol.*). The high-resolution transcriptome study that was done allowed identification of genes with very distinct expression profiles throughout the growth zone. In this disclosure, a chimeric gene was constructed comprising the promoter of a plant GA2 oxidase gene operably coupled to the nucleotide sequence of the KLUH gene. In the exemplified embodiment, it is shown that this chimeric gene—when expressed in a plant—leads to a 30% increase of leaf size. Without limiting the disclosure to a particular mechanism, it is believed that one way this chimeric gene exerts its beneficial action when it is expressed in a plant, is that the expression of the KLUH gene or a functional homologue of at least 55% amino acid identity is prolonged during the growth zone (i.e., the expression of the KLUH gene is kept active for a longer time than the expression of the KLUH gene under control of its own promoter in dividing cells). Further, according to the non-limiting hypothesis, it is thought that the extended (or prolonged) expression of KLUH within the growth zone (as compared to the expression of the KLUH gene under control of its own promoter) results in the stimulation of additional divisions and, consequently, in higher crop yield.

Accordingly, in a first embodiment, the disclosure provides a chimeric gene construct comprising the following operably linked DNA elements: a) the promoter region of a plant GA2 oxidase gene, b) a DNA region encoding a plant CYP78A5 protein or a functional orthologue with an amino acid identity of at least 55%, and c) a 3' end region comprising transcription termination and polyadenylation signals functioning in cells of a plant.

In a particular embodiment, the promoter region of a plant GA2 oxidase gene is active in dividing cells. In yet another particular embodiment, the promoter region of a plant GA2 oxidase gene is active in the growth zone of a plant organ, such as, for example, the leaf. In yet another particular embodiment, the promoter of the plant GA2 oxidase gene is active in the growth zone of the leaf. In yet another particular embodiment, the promoter of the plant GA2 oxidase is active in a plant tissue that is actively dividing. In another particular embodiment, the promoter of the plant GA2 oxidase promoter is active in the cob (of, for example, *Zea mays*). In yet another particular embodiment, the promoter of the plant GA2 oxidase is active in the shoot apical meristem (SAM). In yet another particular embodiment, the promoter of the plant GA2 oxidase is active in the plant embryo.

It is understood that the promoter of the plant GA2 oxidase gene (e.g., organ specific (such as in leaf, cob, embryo or SAM)) is a fragment upstream of the start codon of the gene that consists of about 1000-2500 bp, preferably 1000-2000 bp, more preferably 1000-1500 bp. The GA2 oxidase is known in the art as the gibberellin 2-oxidase. A representative non-limiting example of a GA2 oxidase promoter is depicted in FIG. 1. Other examples of GA2 oxidase promoters are discussed in Example 7 of the disclosure.

The plant KLUH gene is also designated in the art as the CYP78A5. CYP78A5 is a cytochrome P450 oxidase. A representative non-limiting member of the CYP78A5 from corn is depicted in FIG. 2. Other examples of CYP78A5 orthologue genes are described in Example 8 of the disclosure.

In this disclosure, the words "KLUH" or "CYP78A5" are used interchangeably. The terms "KLUH-like" and "CYP78A5-like" are used to define a functional orthologue of KLUH (or CYP78A5). According to the art (D.R. Nelson (2006), *Methods Mol. Biol.* 320:1-10), orthologues of KLUH (or CYP78A5) with an amino acid identity of at least 55% belong to the same functional cluster of cytochrome P450 oxidases and, consequently, have the same function in plants. Thus, in a particular embodiment, a DNA region encoding a plant CYP78A5 protein or a functional orthologue with an amino acid identity of at least 55%, at least 60%, at least 65%, at least 70%, at least 75%, at least 80%, at least 85%, at least 90%, or at least 95% can be used in this disclosure to construct the chimeric gene.

It is understood that a particular chimeric gene can be used as a trait in different plant species and that a plant-specific GA2 oxidase promoter is active in more than one plant species.

In this disclosure, the "plant GA2 oxidase promoter" comprises regulatory elements, which mediate the expression of the KLUH coding sequence segment, or a functional orthologue of at least 55%, at least 60%, at least 65%, at least 70%, at least 75%, at least 80%, at least 85%, at least 90%, or at least 95% identity in plant cells. For expression in plants, the nucleic acid molecule must be linked operably to a suitable plant GA2 oxidase promoter that expresses the KLUH gene or a functional orthologue with at least 55%, at least 60%, at least 65%, at least 70%, at least 75%, at least 80%, at least 85%, at least 90%, or at least 95% at the right point in time and with the required spatial expression pattern in the growth zone (or the cell division zone).

For the identification of functionally equivalent plant GA2 oxidase promoters (for example, in other plant genera or other plant species), the promoter strength and/or expression pattern of a candidate GA2 oxidase promoter may be analyzed, for example, by operably linking the promoter to a reporter gene and assaying the expression level and pattern of the reporter gene in the plant. Suitable well-known reporter genes include, for example, beta-glucuronidase; beta-galactosidase or any fluorescent protein. The promoter activity is assayed by measuring the enzymatic activity of the beta-glucuronidase or beta-galactosidase. Alternatively, promoter strength may also be assayed by quantifying mRNA levels or by comparing mRNA levels of the nucleic acid, with mRNA levels of housekeeping genes such as 18S rRNA, using methods known in the art, such as Northern blotting with densitometric analysis of autoradiograms, quantitative real-time PCR or RT-PCR (Heid et al., 1996, *Genome Methods* 6:986-994).

The term "operably linked" as used herein refers to a functional linkage between the promoter sequence (here, the GA2 oxidase promoter) and the gene of interest (here, the KLUH gene or a functional homologue thereof as defined hereinabove), such that the GA2 oxidase promoter sequence is able to initiate transcription of the KLUH gene (or a functional homologue thereof) of interest.

A "chimeric gene" or "chimeric construct" is a recombinant nucleic acid sequence in which a promoter or regulatory nucleic acid sequence is operatively linked to, or associated with, a nucleic acid sequence that codes for an mRNA, such that the regulatory nucleic acid sequence is able to regulate transcription or expression of the associated nucleic acid coding sequence. The regulatory nucleic acid sequence of the chimeric gene is not normally operatively linked to the associated nucleic acid sequence as found in nature.

The term "terminator" encompasses a control sequence that is a DNA sequence at the end of a transcriptional unit that signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or, alternatively, from another plant gene, or, less preferably, from any other eukaryotic gene.

In yet another embodiment, the disclosure provides a recombinant vector comprising a chimeric gene construct comprising the following operably linked DNA elements: a) the promoter region of a plant GA2 oxidase gene, b) a DNA region encoding a plant CYP78A5 protein or a functional orthologue with an amino acid identity of at least 55%, and c) a 3' end region comprising transcription termination and polyadenylation signals functioning in cells of a plant.

In yet another embodiment, the disclosure provides a plant, plant cell or plant seed comprising a chimeric gene construct comprising the following operably linked DNA elements: a) the promoter region of a plant GA2 oxidase gene, b) a DNA region encoding a plant CYP78A5 protein or a functional orthologue with an amino acid identity of at least 55%, and c) a 3' end region comprising transcription termination and polyadenylation signals functioning in cells of a plant or a recombinant vector comprising a chimeric gene construct comprising the following operably linked DNA elements: a) the promoter region of a plant GA2 oxidase gene, b) a DNA region encoding a plant CYP78A5 protein or a functional orthologue with an amino acid identity of at least 55%, and c) a 3' end region comprising transcription termination and polyadenylation signals functioning in cells of a plant.

In yet another embodiment, the disclosure provides the use of a chimeric gene or a recombinant vector according to the disclosure to increase the yield of plants.

In yet another embodiment, the disclosure provides the use of a chimeric gene or a recombinant vector according to the disclosure to increase the seedling vigor of plants.

In yet another embodiment, the disclosure provides the use of a chimeric gene or a recombinant vector according to the disclosure to increase the drought tolerance of plants. In a specific embodiment, the chimeric gene or recombinant vector comprising the chimeric gene of the disclosure is used to increase the drought tolerance of corn.

In a specific embodiment, the chimeric genes or recombinant vector comprising the chimeric genes are used in crops.

In another specific embodiment, crops are cereals.

In yet another specific embodiment, crops are grasses.

In yet another embodiment, the disclosure provides a method to produce a plant with increased yield as compared to a corresponding wild-type plant, whereby the method comprises introducing or transforming a chimeric gene or a recombinant vector according to the disclosure.

In yet another particular embodiment, the chimeric gene of the disclosure is combined with other chimeric genes that favorably increase the yield of plants. A particular example is the combination of the chimeric GA2ox promoter-KLU gene and the chimeric gene UBIL promoter-GA20oxidase gene in the same corn plant. A specific example of this favorable combination is outlined in Example 5.

The term "yield" as used herein generally refers to a measurable product from a plant, particularly a crop. Yield and yield increase (in comparison to a non-transformed seedling or wild-type plant) can be measured in a number of ways, and it is understood that a skilled person will be able to apply the correct meaning in view of the particular embodiments, the particular crop concerned, and the specific purpose or application concerned. The terms "improved yield" or "increased yield" can be used interchangeably. As used herein, the terms "improved yield" or "increased yield" means any improvement in the yield of any measured plant product, such as grain, fruit, leaf, root, cob or fiber. In accordance with the disclosure, changes in different phenotypic traits may improve yield. For example, and without limitation, parameters such as floral organ development, root initiation, root biomass, seed number, seed weight, harvest index, leaf formation, phototropism, apical dominance, and fruit development, are suitable measurements of improved yield. Increased yield includes higher fruit yields, higher seed yields, higher fresh matter production, and/or higher dry matter production. Any increase in yield is an improved yield in accordance with the disclosure. For example, the improvement in yield can comprise a 0.1%, 0.5%, 1%, 3%, 5%, 10%, 15%, 20%, 30%, 40%, 50%, 60%, 70%, 80%, 90% or greater increase in any measured parameter. For example, an increase in the bu/acre yield of soybeans or corn derived from a crop comprising plants that are transgenic for the chimeric genes of the disclosure, as compared with the bu/acre yield from untransformed soybeans or corn cultivated under the same conditions, is an improved yield in accordance with the disclosure. The increased or improved yield can be achieved in the absence or presence of stress conditions. For example, enhanced or increased "yield" refers to one or more yield parameters selected from the group consisting of biomass yield, dry biomass yield, aerial dry biomass yield, underground dry biomass yield, fresh-weight biomass yield, aerial fresh-weight biomass yield, underground fresh-weight biomass yield; enhanced yield of harvestable parts, either dry, fresh-weight, or both, either aerial, underground, or both; enhanced yield of crop fruit, either dry, fresh-weight, or both, either aerial, underground, or both; and enhanced yield of seeds, either dry, fresh-weight, or both, either aerial, underground, or both.

"Crop yield" is defined herein as the number of bushels of relevant agricultural product (such as grain, forage, or seed) harvested per acre. Crop yield is impacted by abiotic stresses, such as drought, heat, salinity, and cold stress, and by the size (biomass) of the plant. The yield of a plant can depend on the specific plant/crop of interest as well as its intended application (such as food production, feed production, processed food production, biofuel, biogas or alcohol production, or the like) of interest in each particular case. Thus, in one embodiment, yield can be calculated as harvest index (expressed as a ratio of the weight of the respective harvestable parts divided by the total biomass), harvestable parts weight per area (acre, square meter, or the like); and the like. The harvest index is the ratio of yield biomass to the total cumulative biomass at harvest. Harvest index is relatively stable under many environmental conditions, and so a robust correlation between plant size and grain yield is possible.

Measurements of plant size in early development, under standardized conditions in a growth chamber or greenhouse, are standard practices to measure potential yield advantages conferred by the presence of a transgene. Accordingly, the yield of a plant can be increased by improving one or more of the yield-related phenotypes or traits. Such yield-related phenotypes or traits of a plant, the improvement of which results in increased yield, comprise, without limitation, the increase of the intrinsic yield capacity of a plant, improved nutrient use efficiency, and/or increased stress tolerance. For example, yield refers to biomass yield, e.g., to dry weight biomass yield and/or fresh-weight biomass yield. Biomass yield refers to the aerial or underground parts of a plant, depending on the specific circumstances (test conditions, specific crop of interest, application of interest, and the like). In one embodiment, biomass yield refers to the aerial and underground parts. Biomass yield may be calculated as fresh-weight, dry weight or a moisture-adjusted basis. Biomass yield may be calculated on a per plant basis or in relation to a specific area (e.g., biomass yield per acre/square meter/or the like).

"Yield" can also refer to seed yield that can be measured by one or more of the following parameters: number of seeds or number of filled seeds (per plant or per area (acre/square meter/or the like)); seed filling rate (ratio between number of filled seeds and total number of seeds); number of flowers per plant; seed biomass or total seeds weight (per plant or per area (acre/square meter/or the like); thousand kernel weight (TKW; extrapolated from the number of filled seeds counted and their total weight; an increase in TKW may be caused by an increased seed size, an increased seed weight, an increased embryo size, and/or an increased endosperm). Other parameters enabling measurement of seed yield are also known in the art. Seed yield may be determined on a dry weight or on a fresh weight basis, or typically on a moisture-adjusted basis, e.g., at 15.5 percent moisture. For example, the term "increased yield" means that a plant exhibits an increased growth rate, e.g., in the absence or presence of abiotic environmental stress, compared to the corresponding wild-type plant. An increased growth rate may be reflected inter alia by or confers an increased biomass production of the whole plant, or an increased biomass production of the aerial parts of a plant, or by an increased biomass production of the underground parts of a plant, or by an increased biomass production of parts of a plant, like stems, leaves, blossoms, fruits, and/or seeds. A prolonged growth comprises survival and/or continued growth of the plant, at the moment when the non-transformed wild-type organism shows visual symptoms of deficiency and/or death. When the plant of the disclosure is a corn plant, increased yield for corn plants means, for example, increased seed yield, in particular, for corn varieties used for feed or food. Increased seed yield of corn refers to an increased kernel size or weight, an increased kernel per ear, or increased ears per plant. Alternatively, or in addition, the cob yield may be increased, or the length or size of the cob is increased, or the kernel per cob ratio is improved.

When the plant of the disclosure is a soy plant, increased yield for soy plants means increased seed yield, in particular, for soy varieties used for feed or food. Increased seed yield of soy refers, for example, to an increased kernel size or weight, an increased kernel per pod, or increased pods per plant. When the plant of the disclosure is an oil seed rape (OSR) plant, increased yield for OSR plants means increased seed yield, in particular, for OSR varieties used for feed or food. Increased seed yield of OSR refers to an increased seed size or weight, an increased seed number per silique, or increased siliques per plant. When the plant of the disclosure is a cotton plant, increased yield for cotton plants means increased lint yield. Increased lint yield of cotton refers in one embodiment to an increased length of lint. When the plant is a plant belonging to grasses, an increased leaf can mean an increased leaf biomass. The increased yield can typically be achieved by enhancing or improving one or more yield-related traits of the plant. Such yield-related traits of a plant comprise, without limitation, the increase of the intrinsic yield capacity of a plant, improved nutrient use efficiency, and/or increased stress tolerance, in particular, increased abiotic stress tolerance. Intrinsic yield capacity of a plant can be, for example, manifested by improving the specific (intrinsic) seed yield (e.g., in terms of increased seed/grain size, increased ear number, increased seed number per ear, improvement of seed filling, improvement of seed composition, embryo and/or endosperm improvements, or the like); modification and improvement of inherent growth and development mechanisms of a plant (such as plant height, plant growth rate, pod number, pod position on the plant, number of internodes, incidence of pod shatter, efficiency of nodulation and nitrogen fixation, efficiency of carbon assimilation, improvement of seedling vigor/early vigor, enhanced efficiency of germination (under stressed or non-stressed conditions), improvement in plant architecture, cell cycle modifications, photosynthesis modifications, various signaling pathway modifications, modification of transcriptional regulation, modification of translational regulation, modification of enzyme activities, and the like); and/or the like.

"Selectable marker," "selectable marker gene" or "reporter gene" includes any gene that confers a phenotype on a cell in which it is expressed to facilitate the identification and/or selection of cells that are transfected or transformed with a nucleic acid construct of the disclosure. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracycline, chloramphenicol, ampicillin, gentamycin, geneticin (0418), spectinomycin or blasticidin), to herbicides (for example, bar that provides resistance to BASTA®), aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilization of xylose, or antinutritive markers such as the resistance to 2-deoxyglucose). Expression of visual marker genes results in the formation of color (for example, β-glucuronidase, GUS or β-galactosidase with its colored substrates, for example, X-Gal), luminescence (such as the luciferin/luciferase system) or fluorescence (Green Fluorescent Protein, GFP, and derivatives thereof). This list represents only a small number of possible markers. The skilled worker is familiar with such markers. Different markers are preferred, depending on the organism and the selection method.

It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can, for example, be used in mutants in which these genes are not functional by, for example, deletion by conventional methods. Furthermore, nucleic acid molecules encoding a selectable marker can be introduced into a host cell on the same vector that comprises the sequence encoding the polypeptides of the disclosure or used in the methods of the disclosure, or else in a separate vector. Cells that have been stably transfected with the introduced nucleic acid can be identified, for example, by selection (for example, cells that have integrated the selectable marker survive, whereas the other cells die).

Since the marker genes, particularly genes for resistance to antibiotics and herbicides, are no longer required or are undesired in the transgenic host cell once the nucleic acids have been introduced successfully, the process according to the disclosure for introducing the nucleic acids advantageously employs techniques that enable the removal or excision of these marker genes. One such method is what is known as co-transformation. The co-transformation method employs two vectors simultaneously for the transformation, one vector bearing the nucleic acid according to the disclosure and a second bearing the marker gene(s). A large proportion of transformants receives or, in the case of plants, comprises (up to 40% or more of the transformants), both vectors. In the case of transformation with Agrobacteria, the transformants usually receive only a part of the vector, i.e., the sequence flanked by the T-DNA, which usually represents the expression cassette. The marker genes can subsequently be removed from the transformed plant by performing crosses. In another method, marker genes integrated into a transposon are used for the transformation, together with desired nucleic acid (known as the Ac/Ds technology). The transformants can be crossed with a transposase source or the transformants are transformed with a nucleic acid construct conferring expression of a transposase, transiently or stable. In some cases (approximately 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed that make possible, or facilitate, the detection of such events. A further advantageous method relies on what is known as "recombination systems," whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has successfully taken place by expression of the recombinase. Further recombination systems are the HIN/HIX, FLP/FRT and REP/STB system (Tribble et al., *J. Biol. Chem.* 2000, 275:22255-22267; Velmurugan et al., *J. Cell. Biol.* 2000, 149:-553-566). A site-specific integration into the plant genome of the nucleic acid sequences according to the disclosure is possible.

For the purposes of the disclosure, "transgenic," "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the disclosure.

A transgenic plant for the purposes of the disclosure is thus understood as meaning, as above, that the nucleic acids used in the method of the disclosure are not present in, or originating from, the genome of the plant, or are present in the genome of the plant but not at their natural locus in the genome of the plant, it being possible for the nucleic acids to be expressed homologously or heterologously. However, as mentioned, transgenic also means that, while the nucleic acids according to the disclosure or used in the disclosed method are at their natural position in the genome of a plant, the sequence has been modified with regard to the natural sequence, and/or that the regulatory sequences of the natural sequences have been modified. Transgenic is preferably understood as meaning the expression of the nucleic acids according to the disclosure at an unnatural locus in the genome, i.e., homologous or, heterologous expression of the nucleic acids takes place. Preferred transgenic plants are mentioned herein.

For the purpose of this disclosure, related or orthologous genes of the KLUH gene as described hereinbefore can be isolated from the (publically) available sequence databases. The "sequence identity" of two related nucleotide or amino acid sequences, expressed as a percentage, refers to the number of positions in the two optimally aligned sequences that have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch (1970) *J. Mol. Biol.* 48:443-453). The computer-assisted sequence alignment above can be conveniently performed using a standard software program such as GAP, which is part of the Wisconsin Package Version 10.1 (Genetics Computer Group, Madison, Wis., USA) using the default scoring matrix with a gap creation penalty of 50 and a gap extension penalty of 3. Sequences are indicated as "essentially similar" when such sequences have a sequence identity of at least about 75%, particularly at least about 80%, more particularly at least about 85%, quite particularly about 90%, especially about 95%, more especially about 100%, quite especially are identical.

Alternatively, the skilled person can isolate orthologous plant KLUH genes through methods of genetic hybridization. Such methods are well known to the skilled (plant) molecular biologist.

The term "expression" or "gene expression" means the transcription of a specific gene or specific genes or specific genetic construct. The term "expression" or "gene expression," in particular, means the transcription of a gene or genes or genetic construct into structural RNA (rRNA, tRNA) or mRNA with or without subsequent translation of the latter into a protein. The process includes transcription of DNA and processing of the resulting mRNA product.

The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of this disclosure and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen, and microprojection. Methods may be selected from the calcium/polyethylene glycol method for protoplasts (F. A. Krens et al. (1982) *Nature* 296:72-74; I. Negrutiu et al. (1987) *Plant Mol. Biol.* 8:363-373); electroporation of protoplasts (R. D. Shillito et al. (1985) *Bio./Technol.* 3:1099-1102); microinjection into plant material (A. Crossway et al. (1986) *Mol. Gen. Genet.* 202:179-185); DNA or RNA-coated particle bombardment (T. M. Klein et al. (1987) *Nature* 327:70) infection with (non-integrative) viruses, and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the disclosure to allow a suspension of transformed agrobacteria to act on the intact plant or at least on the flower primordia. The plant is subsequently grown until the seeds of the treated plant are obtained (Clough and Bent, *Plant J* (1998) 16:735-743). Methods for *Agrobacterium*-mediated transformation of rice include well-known methods for rice transformation, such as those described in any of the following: European patent application EP1198985, Aldemita and Hodges (*Planta* 199:612-617, 1996); Chan et al. (*Plant Mol. Biol.* 22 (3):491-506, 1993), Hiei et al. (*Plant J.* 6 (2):271-282, 1994), which disclosures are incorporated by reference herein as if fully set forth. In the case of corn transformation, the preferred method is as described in either Ishida et al. (*Nat. Biotechnol.* 14(6):745-50, 1996) or Frame et al. (*Plant Physiol.* 129(1):13-22, 2002), which disclosures are incorporated by reference herein as if fully set forth. These methods are further described by way of example in B. Jenes et al., "Techniques for Gene Transfer" in *Transgenic Plants*, Vol. 1, *Engineering and Utilization*, eds. S. D. Kung and R. Wu, Academic Press (1993) 128-143, and in Potrykus, *Annu. Rev. Plant Physiol. Plant Molec. Biol.* (1991) 42:205-225). The nucleic acids or the construct to be expressed is preferably cloned into a vector, which is suitable for transforming *Agrobacterium tumefaciens*, for example, pBin19 (Bevan et al. (1984) *Nucl. Acids Res.* 12-8711). Agrobacteria transformed by such a vector can then be used in known manner for the transformation of plants, such as plants used as a model, like *Arabidopsis* (*Arabidopsis thaliana* is within the scope of this disclosure not considered as a crop plant), or crop plants such as, by way of example, tobacco plants, for example, by immersing bruised leaves or chopped leaves in an agrobacterial solution and then culturing them in suitable media. The transformation of plants by means of *Agrobacterium tumefaciens* is described, for example, by Hofgen and Willmitzer in *Nucl. Acid. Res.* (1988) 16:9877, or is known inter alia from F. F. White, "Vectors for Gene Transfer in Higher Plants" in *Transgenic Plants*, Vol. 1, *Engineering and Utilization*, eds. S. D. Kung and R. Wu, Academic Press, 1993, pp. 15-38.

In addition to the transformation of somatic cells, which then have to be regenerated into intact plants, it is also possible to transform the cells of plant meristems and, in particular, those cells that develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic (K. A. Feldman and M. D. Marks (1987) *Mol. Gen. Genet.* 208:1-9; K. Feldmann (1992) in C. Koncz, N-H Chua and J. Shell, eds, *Methods in Arabidopsis Research*, Word Scientific, Singapore, pp. 274-289). Alternative methods are based on the repeated removal of the inflorescences and incubation of the excision site in the center of the rosette with transformed agrobacteria, whereby transformed seeds can likewise be obtained at a later point in time (Chang (1994) *Plant J.* 5:551-558; Katavic (1994) *Mol. Gen. Genet.* 245:363-370). However, an especially effective method is the vacuum infiltration method with its modifications such as the "floral dip" method. In the case of vacuum infiltration of *Arabidopsis*, intact plants under reduced pressure are treated with an agrobacterial suspension (N. Bechthold (1993) *C. R. Acad. Sci. Paris Life Sci.* 316:1194-1199), while in the case of the "floral dip" method, the developing floral tissue is incubated briefly with a surfactant-treated agrobacterial suspension (S. J. Clough and A. F. Bent (1998) *The Plant J.* 16:735-743). A certain proportion of transgenic seeds are harvested in both cases, and these seeds can be distinguished from non-transgenic seeds by growing under the above-described selective conditions. In addition, the stable transformation of plastids is advantageous because plastids are inherited maternally in most crops reducing or eliminating the risk of transgene flow through pollen. The transformation of the chloroplast genome is generally achieved by a process that has been schematically displayed in Klaus et al., 2004 (*Nature Biotechnology* 22 (2):225-229). Briefly, the sequences to be transformed are cloned together with a selectable marker gene between flanking sequences homologous to the chloroplast genome. These homologous flanking sequences direct site-specific integration into the plastome. Plastidal transformation has been described for many different plant species and an overview is given in Bock (2001) Transgenic plastids in basic research and plant biotechnology, *J. Mol. Biol.* 2001 Sep. 21 312 (3):425-38, or P. Maliga (2003) Progress towards commercialization of plastid transformation technology, *Trends Biotechnol.* 21:20-28. Further, biotechnological progress has recently been reported in the form of marker-free plastid transformants, which can be produced by a transient co-integrated marker gene (Klaus et al., 2004, *Nature Bioltechnology* 22(2):225-229).

The genetically modified plant cells can be regenerated via all methods with which the skilled worker is familiar. Suitable methods can be found in the above-mentioned publications by S. D. Kung and R. Wu, Potrykus or Hofgen and Willmitzer.

Generally after transformation, plant cells or cell groupings are selected for the presence of one or more markers that are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance, using Southern analysis, for the presence of the gene of interest, copy number and/or genomic organization. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells, clonal transformants (e.g., all cells transformed to contain the expression cassette), and grafts of transformed and untransformed tissues (e.g., in plants, a transformed rootstock grafted to an untransformed scion).

The terms "increase," "improve" or "enhance" are interchangeable and shall mean in the sense of the application at least a 3%, 4%, 5%, 6%, 7%, 8%, 9% or 10%, preferably at least 15% or 20%, more preferably 25%, 30%, 35%, 40%, 50%, 60%, 70%, 80%, 90%, 95% or more yield and/or growth in comparison to control plants as defined herein.

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the disclosure include, in particular, monocotyledonous and dicotyledonous plants including fodder or forage legumes, ornamental plants, food crops, trees or shrubs selected from the list comprising Acer spp., Actinidia spp., Abelmoschus spp., Agave sisalana, Agropyron spp., Agrostis stolonifera, Allium spp., Amaranthus spp., Ammophila arenaria, Ananas comosus, Annona spp., Apium graveolens, Arachis spp, Artocarpus spp., Asparagus officinalis, Avena spp. (e.g., Avena sativa, Avena fatua, Avena byzantina, Avena fatua var. sativa, Avena hybrida), Averrhoa carambola, Bambusa sp., Benincasa hispida, Bertholletia excelsea, Beta vulgaris, Brassica spp. (e.g., Brassica napus, Brassica rapa ssp. (canola, oilseed rape, turnip rape)), Cadaba farinosa, Camellia sinensis, Canna indica, Cannabis sativa, Capsicum spp., Carex elata, Carica papaya, Carissa macrocarpa, Carya spp., Carthamus tinctorius, Castanea spp., Ceiba pentandra, Cichorium endivia, Cinnamomum spp., Citrullus lanatus, Citrus spp., Cocos spp., Coffea spp., Colocasia esculenta, Cola spp., Corchorus sp., Coriandrum sativum, Corylus spp., Crataegus spp., Crocus sativus, Cucurbita spp., Cucumis spp., Cynara spp., Daucus carota, Desmodium spp., Dimocarpus longan, Dioscorea spp., Diospyros spp., Echinochloa spp., Elaeis (e.g., Elaeis guineensis, Elaeis oleifera), Eleusine coracana, Eragrostis tef, Erianthus sp., Eriobotrya japonica, Eucalyptus sp., Eugenia uniflora, Fagopyrum spp., Fagus spp., Festuca arundinacea, Ficus carica, Fortunella spp., Fragaria spp., Ginkgo biloba, Glycine spp. (e.g., Glycine max, Soja hispida or Soja max), Gossypium hirsutum, Helianthus spp. (e.g., Helianthus annuus), Hemerocallis fulva, Hibiscus spp., Hordeum spp. (e.g., Hordeum vulgare), Ipomoea batatas, Juglans spp., Lactuca sativa, Lathyrus spp., Lens culinaris, Linum usitatissimum, Litchi chinensis, Lotus spp., Luffa acutangula, Lupinus spp., Luzula sylvatica, Lycopersicon spp. (e.g., Lycopersicon esculentum, Lycopersicon lycopersicum, Lycopersicon pyriforme), Macrotyloma spp., Malus spp., Malpighia emarginata, Mammea americana, Mangifera indica, Manihot spp., Manilkara zapota, Medicago sativa, Melilotus spp., Mentha spp., Miscanthus sinensis, Momordica spp., Morus nigra, Musa spp., Nicotiana spp., Olea spp., Opuntia spp., Ornithopus spp., Oryza spp. (e.g., Oryza sativa, Oryza latifolia), Panicum miliaceum, Panicum virgatum, Passiflora edulis, Pastinaca sativa, Pennisetum sp., Persea spp., Petroselinum crispum, Phalaris arundinacea, Phaseolus spp., Phleum pratense, Phoenix spp., Phragmites australis, Physalis spp., Pinus spp., Pistacia vera, Pisum spp., Poa spp., Populus spp., Prosopis spp., Prunus spp., Psidium spp., Punica granatum, Pyrus communis, Quercus spp., Raphanus sativus, Rheum rhabarbarum, Ribes spp., Ricinus communis, Rubus spp., Saccharum spp., Salix sp., Sambucus spp., Secale cereale, Sesamum spp., Sinapis sp., Solanum spp. (e.g., Solanum tuberosum, Solanum integrifolium or Solanum lycopersicum), Sorghum bicolor, Spinacia spp., Syzygium spp., Tagetes spp., Tamarindus indica, Theobroma cacao, Trifolium spp., Tripsacum dactyloides, Triticosecale rimpaui, Triticum spp. (e.g., Triticum aestivum, Triticum durum, Triticum turgidum, Triticum hybernum, Triticum macha, Triticum sativum, Triticum monococcum or Triticum vulgare), Tropaeolum minus, Tropaeolum majus, Vaccinium spp., Vicia spp., Vigna spp., Viola odorata, Vitis spp., Zea mays, Zizania palustris, Ziziphus spp., amongst others.

The choice of suitable control plants is a routine part of an experimental setup and may include corresponding wild-type plants or corresponding plants without the gene of interest. The control plant is typically of the same plant species or even of the same variety as the plant to be assessed. The control plant may also be a nullizygote of the plant to be assessed. Nullizygotes are individuals missing the transgene by segregation. A "control plant" as used herein refers not only to whole plants, but also to plant parts, including seeds and seed parts.

The term "expression cassette" refers to any recombinant expression system for the purpose of expressing a nucleic acid sequence of the disclosure in vitro or in vivo, constitutively or inducibly, in any cell, including, in addition to plant cells, prokaryotic, yeast, fungal, insect or mammalian cells. The term includes linear and circular expression systems. The term includes all vectors. The cassettes can remain episomal or integrate into the host cell genome. The expression cassettes can have the ability to self-replicate or not (i.e., drive only transient expression in a cell). The term includes recombinant expression cassettes that contain only the minimum elements needed for transcription of the recombinant nucleic acid.

The following non-limiting examples describe methods and means according to the disclosure. Unless stated otherwise in the examples, all techniques are carried out according to protocols standard in the art. The following examples are included to illustrate embodiments of the disclosure. Those of skill in the art should, in light of the present disclosure, appreciate that many changes can be made in the specific embodiments that are disclosed and still obtain a like or similar result without departing from the concept, spirit and scope of the disclosure. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

EXAMPLES

1. Construction of a Chimeric Gene: GA2 Oxidase Promoter Operably Linked to a KLUH Coding Sequence The corn GA2 oxidase promoter derived from the *Zea mays* GRMZM2G031724 gene was isolated (2046 bp) and fused with attB4 and attB1r sites, and combined with entry vector pDONR P4-P1r by BP reaction (see FIG. 1).

A representative corn KLUH (GRMZM2G167986) gene was also isolated. The gene has one intron, leads to two transcript patterns in maize. The genome sequence (1834 bp) was isolated, including intron and coding sequence (CDS). The KLUH sequence was fused with attB1 and attB2 sites, and combined with entry vector pDONR 221 by BP reaction (see FIG. 2).

Figure 4:
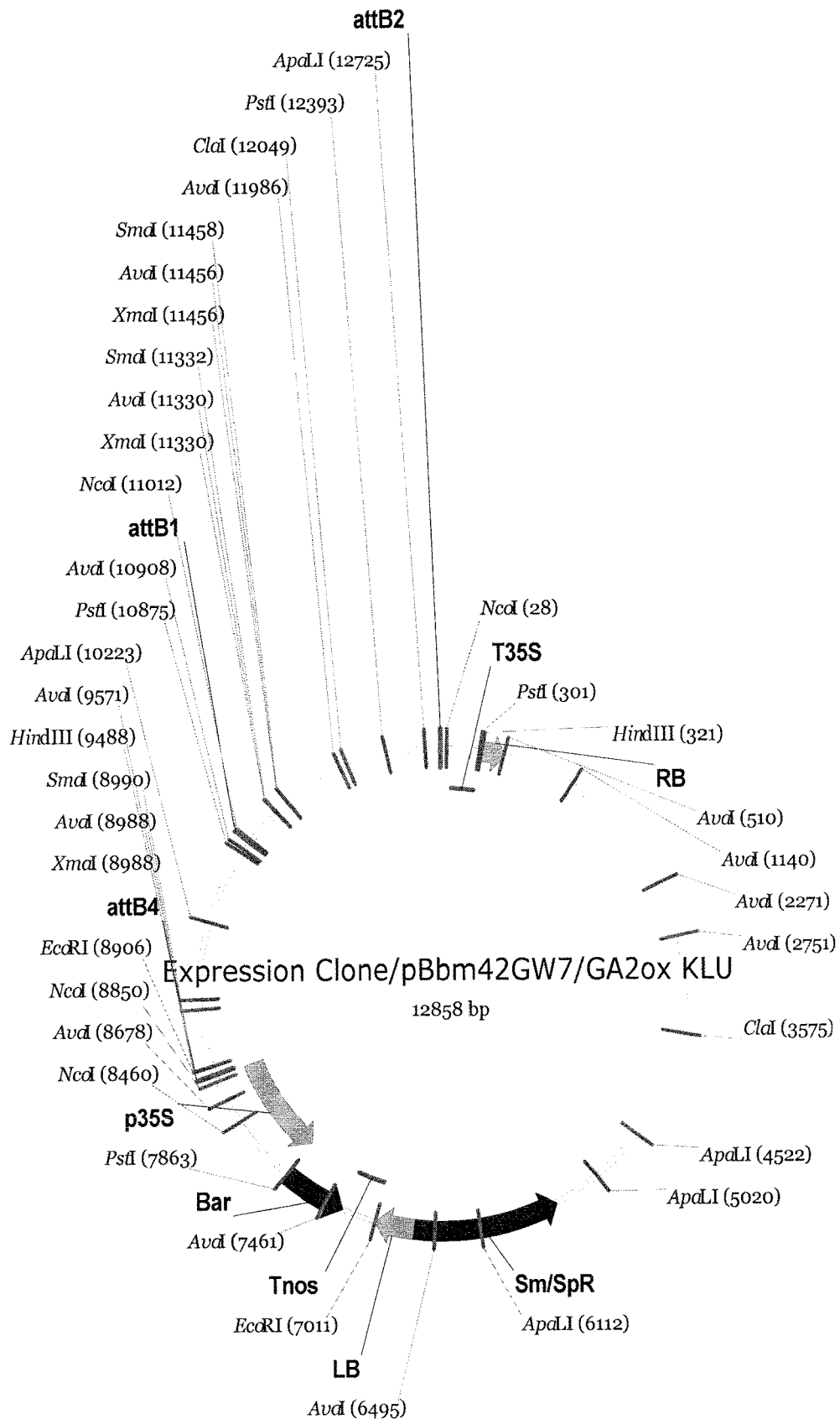
FIG. 4: Structure of expression clone containing GA2 oxidase promoter and KLUH gene.

Expression vector pBb42GW7 is a MultiSite Gateway intermediary vector designed for monocot ((Karimi et al., 2013); see FIG. 3). GA2 oxidase promoter operably linked to the KLUH gene was inserted into expression vector pBb42GW7 through LR reaction between attR4 and attR2. Bar gene driven by 35S promoter was used for selecting transgenic plants during the transformation process (see FIG. 4). The sequence of the chimeric gene of the GA2 oxidase promoter operably linked to the KLUH gene in expression vector pBb42GW7 is shown in FIG. 5.

Maize transformation was performed according to Coussens et al. (2012).

In total, ten independent T0 lines were obtained after transformation. Around 35 T1 seeds from T0 backcrossed with wild-type B104 were sown in soil for segregation analysis and phenotyping. Ammonium assay (De Block et al., 1995) was used to detect transgenic plants; leaf painting was used to confirm certain plants for upscaling.

Four independent lines 139_01, 140_01, 140_04, 140_05, which have one T-DNA insertion and showed a phenotype, were selected for further analysis (see Table 1).

TABLE 1

Chi square test and phenotyping results of T1 plants.

| | Resistance plants | Sensitive plants | NA plants | Chi$^2$ value | Phenotype |
|---|---|---|---|---|---|
| 139_01 | 14 | 13 | 8 | 0.037* | Yes |
| 139_04 | 20 | 10 | 5 | 3.33 | |
| 139_05 | 17 | 13 | 5 | 0.53* | |
| 139_07 | 19 | 9 | 7 | 3.57 | Yes |
| 140_01 | 15 | 12 | 8 | 0.33* | Yes |
| 140_04 | 19 | 10 | 3 | 2.79* | Yes |
| 140_05 | 11 | 19 | 2 | 2.13* | Yes |
| 140_07 | 20 | 12 | 0 | 2* | |
| 140_09 | 13 | 8 | 9 | 1.19* | |
| 140_11 | 22 | 6 | 2 | 9.14 | Yes |

*indicates single locus lines.
NA plants could not be genotyped due to late germination or retarded growth.

2. Phenotypical and Molecular Analysis of the Corn Transformants Comprising the Chimeric Gene Leaf length of plants was measured from the top of soil to the leaf tip. The leaf length and leaf area of leaf 2 were measured when they were fully grown (two days after leaf 4 appears). The length of leaf 4 was measured daily from leaf 4 appearance until they were fully grown (around 10 days). From leaf 4 recorded data, LER is calculated as the difference in leaf length on two successive time-points divided by the time interval between them (in mm/hr). The area of leaf 4 was measured when the leaf was fully grown. The leaf blade was scanned and leaf area was calculated using Image J. The kinematic analysis was performed as described in (Nelissen et al., 2013).

Figure 6:
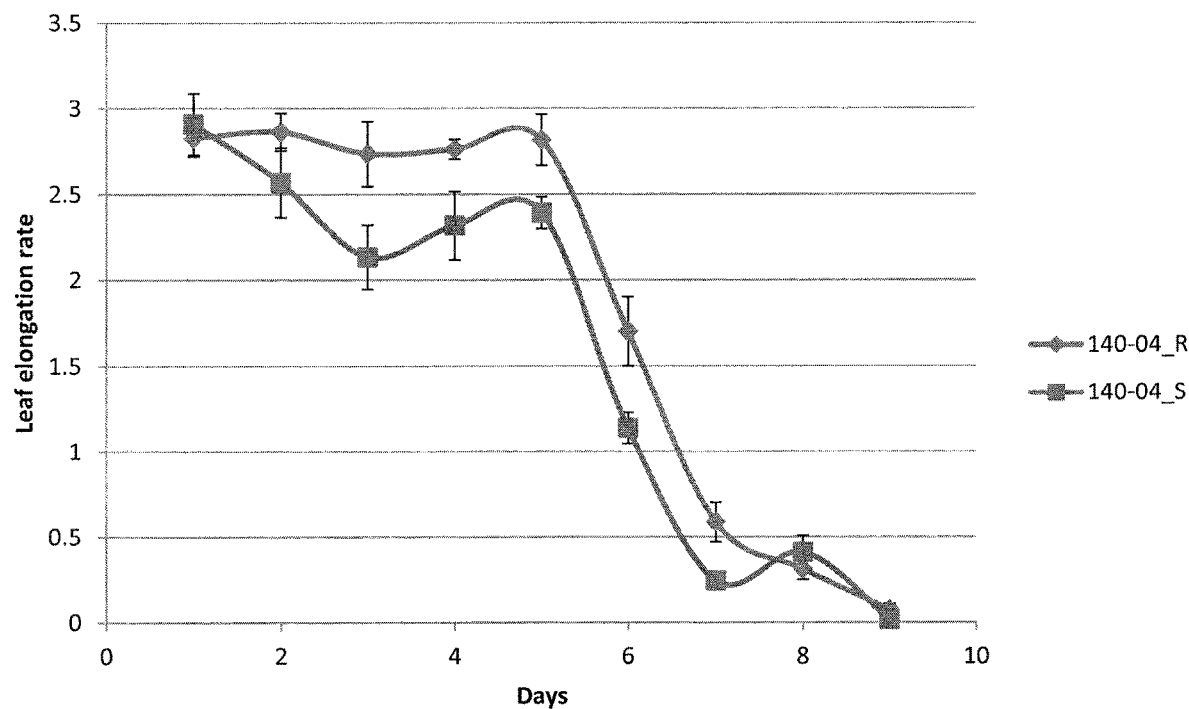
FIG. 6: Leaf elongation rate in 140_04. R represents transgenic (resistant) plants; S represents non-transgenic (sensitive) plants.
Figure 7:
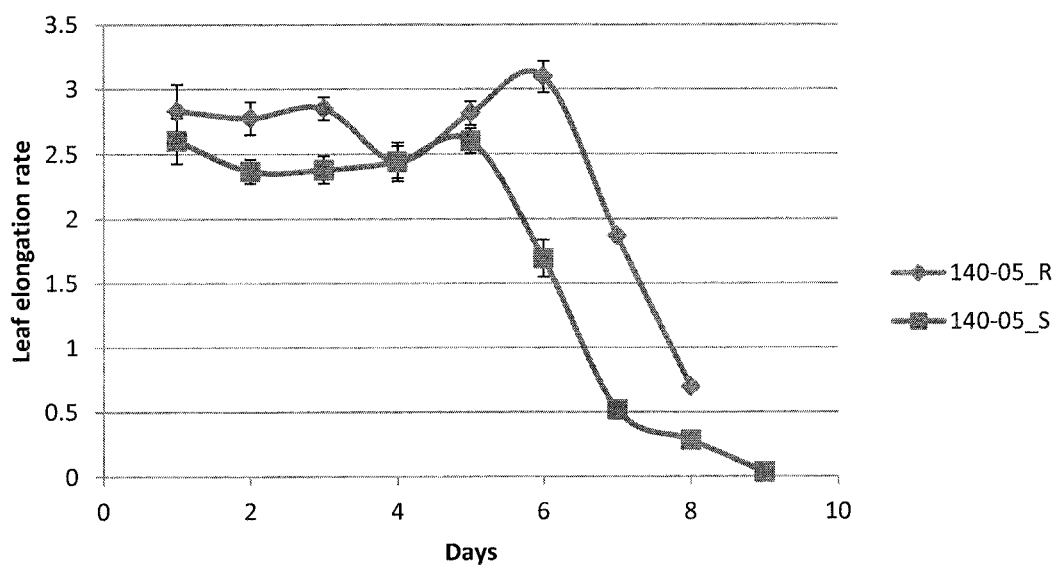
FIG. 7: Leaf elongation rate in 140_05. R represents transgenic (resistant) plants; S represents non-transgenic (sensitive) plants.

By now, part of leaf measurements has been done in four selected lines. Final leaf length and leaf area of leaf 2 were calculated in 140_01 and 139_01 (Table 2). Leaf elongation rate and more detailed leaf 4 parameters were calculated in 140_04 and 140_05 (FIG. 6, Table 3, FIG. 7, Table 4).

2.1 Leaf 2 Parameters for Lines 140_01 and 139_01 Show Increased Leaf Length and area For lines 140_01 and 139_01, only measurements on fully grown leaf 2 were done until now. However, they show that the final leaf area and length is significantly increased in the two independent lines. The leaf 4 parameters are currently being measured in these two lines.

TABLE 2

Leaf parameters of leaf 2 of two T1 lines 140_01 and 139_01.

| | 140-01 | | | | 139-01 | | | |
|---|---|---|---|---|---|---|---|---|
| | R | S | Δ% | P_value | R | S | Δ% | P_value |
| leaf area (mm^2) | 1807.7 | 1276.9 | 29.4 | 0 | 1932.9 | 1236.3 | 36 | 0.006 |
| Internode (mm) | 105 | 90.5 | 13.8 | 0.003 | 105 | 97.5 | 7.1 | 0.19 |
| leaf length (mm) | 293.8 | 223.5 | 23.9 | 0.0008 | 298.3 | 234.8 | 21.3 | 0.021 |
| leaf width (mm) | 13.8 | 12.5 | 9.2 | 0.006 | 13 | 11.7 | 10 | 0.11 |

R represents transgenic (resistant) plants;
S represents non-transgenic (sensitive) plants.

2.2 Leaf 4 Parameters for Lines 140_04 and 140_05 Show Increased LER, Leaf Length and size of the division zone For lines 140_04 and 140_05, the length of leaf 4 was monitored while it was growing, showing that the leaf elongation rate (LER) was higher during the steady state in the transgenic versus control plants and that the duration of growth was increased in the transgenic line (FIGS. 6 and 7).

In addition, when measurements were performed on two plants per line, it was clear that the area was increased by 34%-45% (Tables 3 and 4). For leaf length and the size of the division zone, more plants were analyzed, allowing statistical analysis: the final leaf length of leaf 4 was significantly increased in both transgenic lines (ranging from 15.3% to 24.2%). For line 140_04, a preliminary measurement of the size of the division zone was determined showing that the increase in leaf length in that line was at least in part due to an increased size of the division zone (15.7%) and, thus, the number of dividing cells (Table 3).

TABLE 3

Leaf parameters of leaf 4 of 140_04.

| 140_04 | Leaf 4 area | Leaf 4 length | leaf 4 width | DZ size |
|---|---|---|---|---|
| R | 53.6 | 65.3 | 2.3 | 1.8 |
| S | 35.5 | 49.5 | 1.9 | 1.5 |
| Δ % | 33.9 | 24.2 | 17.2 | 15.7 |
| P-value | | 0.005 | | 0.02 |

R represents transgenic (resistant) plants;
S represents non-transgenic (sensitive) plants.

TABLE 4

Leaf parameters of leaf 4 of 140_05.

| 140_05 | Leaf 4 area | Leaf 4 length | leaf 4 width |
|---|---|---|---|
| R | 77.1 | 64.5 | 2.3 |
| S | 41.9 | 54.6 | 1.8 |
| Δ % | 45.6 | 15.3 | 22.4 |
| p-value | | 0.04 | |

R represents transgenic (resistant) plants;
S represents non-transgenic(sensitive) plants.

Figure 8:
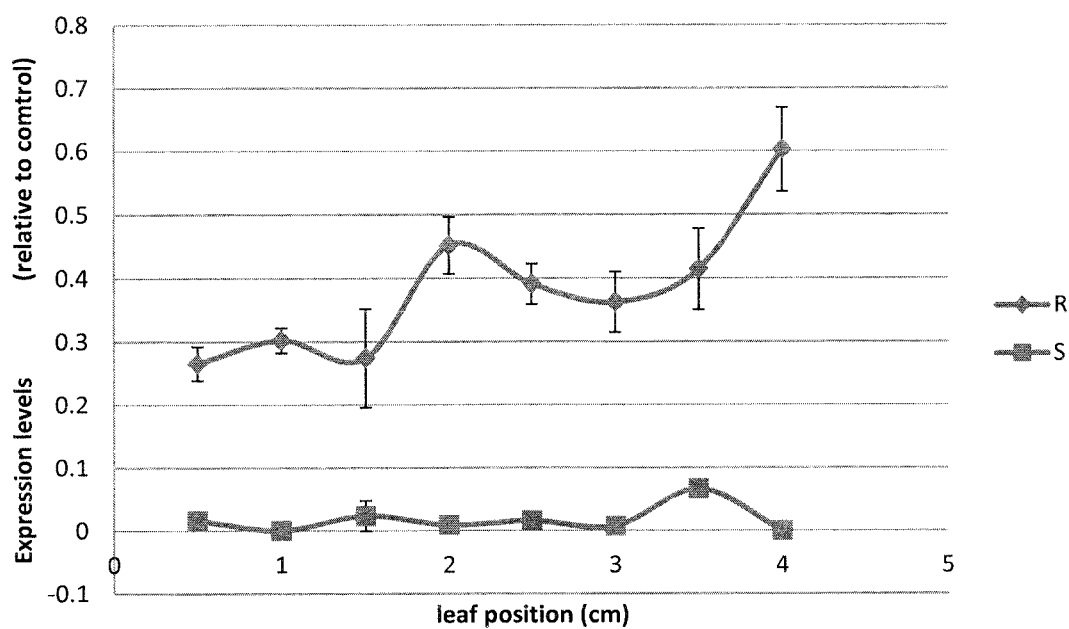
FIG. 8: Comparative KLUH expression results of leaf 4 of 140_01. R represents transgenic plants; S represents non-transgenic plants.
Figure 9:
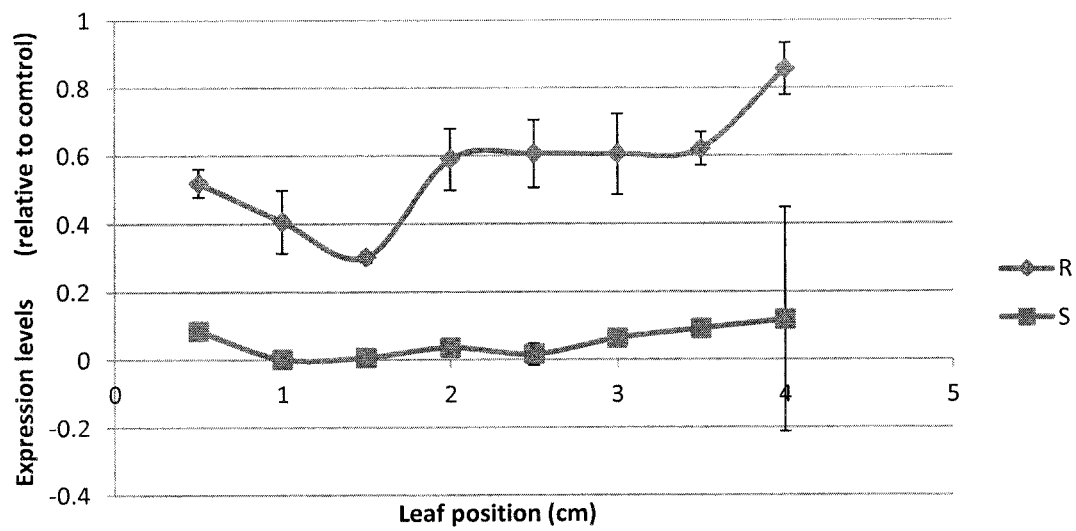
FIG. 9: Comparative KLUH expression results of leaf 4 of 139_01. R represents transgenic plants; S represents non-transgenic plants.

2.3 QPCR Analysis Shows Higher Expression of KLUH in the Growth Zone of the Maize Leaf Leaf 4 was harvested two days after they appeared to analyze KLUH overexpression level under GA2 oxidase promoter. Leaf 4 was cut into ten pieces from leaf base toward leaf tip at 0.5 cm scale. From qPCR analysis, two lines showed larger leaf 2 phenotype, 140_01 and 139_01, have higher expression level of KLUH compared to non-transgenic plants (FIGS. 8 and 9).

2.4 Conclusion

From the ten transformation events, four lines were chosen in which the T-DNA was inserted in a single locus in the genome. All four lines show leaf growth enhancement, resulting in longer leaves with increased blade area. This increased leaf blade area enables the capture of more sunlight, which can result in more net photosynthesis to take place. Cellular analysis of one line showed that the increased leaf length is, at least in part, due to an increase in the size of the division zone, thus more dividing cells. While not intending to limit the disclosure to a particular mechanism, one hypothesis is that since KLUH was shown to stimulate cell division in plants and thus extending the expression of KLUH within the growth zone, results in the stimulation of additional divisions (in a particular plant organ).

The four lines are now grown next to each other and detailed leaf 4 measurements will be performed. In the same experiment, a comparison is performed of the "overexpression" levels of KLUH in the growth zone. The plants are also grown until maturity to assess final plant height, flowering time, anthesis-silking-interval (ASI), seed yield, biomass, and internode length.

Figure 10:
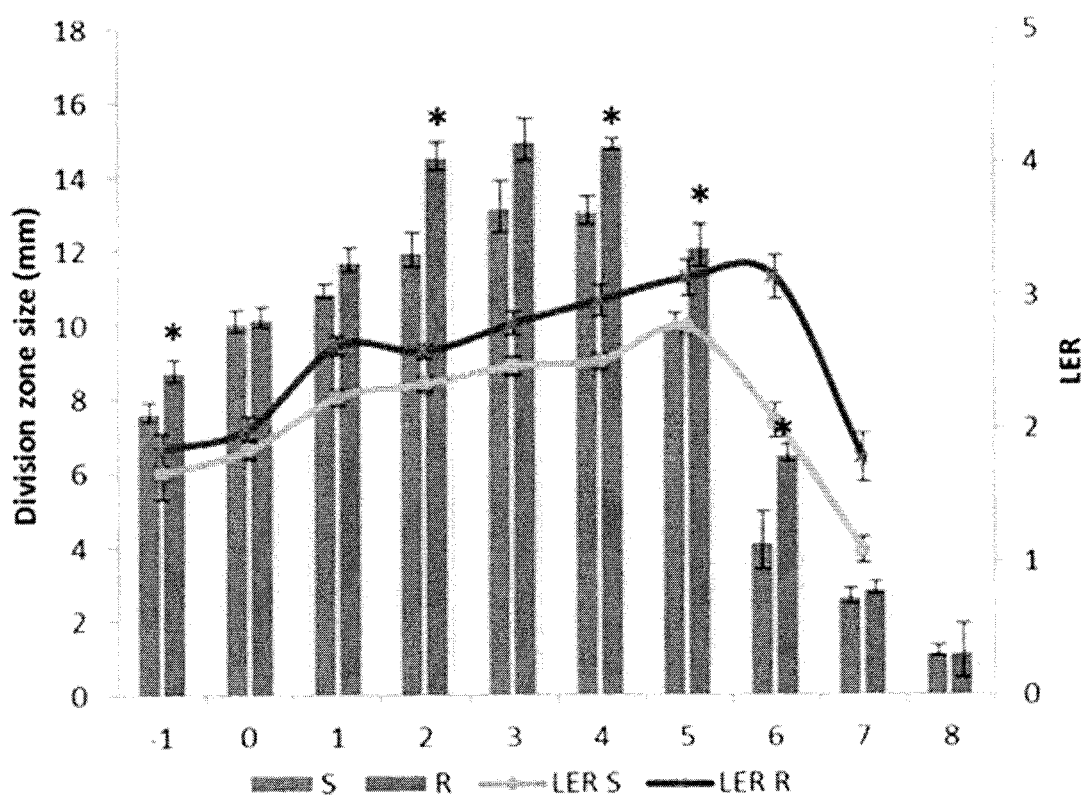
FIG. 10: Division zone size timing in GA2ox::KLUH. The bar graph shows how the size of the division zone changed during leaf 4 growth. The linear graph showed leaf elongation rate of leaf 4 at the same time points. S indicates wild-type (left bars); R indicates resistant plants of transgenic GA2ox::KLUH (right bars); asterisks indicate p<0.01.

3. Corn Plants Genetically Transformed with the Chimeric Gene GA2ox::KLUH have a Stable Division Zone for at Least One Extra Day Detailed kinematic analysis over time was applied on leaf 4. From several independent transformed plants, leaf 4 was harvested every day since it emerged from leaf 3 until it was fully grown. The size of the division zone was determined by DAPI staining. A significant interaction between the division zone size and the time of leaf growth was shown by ANOVA, showing that the division zone size in GA2ox::KLUH remained one day longer at maximal size than wild-type (see day 5 in FIG. 10).

4. Transgenic Corn Plants Harboring the Chimeric Gene GA2ox::KLUH have Shorter Anthesis Silking Interval than Wild-Type An average three days shorter anthesis silking (ASI) interval was observed in the transgenic corn plants harboring the chimeric gene GA2ox::KLUH compared to wild-type corn plants. ASI is the time in between pollen shedding and the appearance of the silk. The shorter ASI enables more viable pollen to get into the silk to facilitate pollination efficiency and it is also documented in the art that it can help plants to maintain yield under drought stress.

5. Hybrid Transgenic Corn Plants Harboring a Chimeric GA2ox::KLUH Gene and a Chimeric UBIL::GA20ox Gene have a Higher Biomass Yield than their Parents Previously, it was shown that in the transgenic corn plants harboring the chimeric gene UBIL::GA20Ox, the high levels of GA mainly affect the maximal levels of growth rate (LER), but not the timing of growth (see Nelissen et al., 2012). In this disclosure, it is shown that corn plants harboring the chimeric gene GA2OX::KLUH minimally affect the maximal growth rate, but that the presence of this chimeric gene keeps the growth rate maximal for an additional day, i.e., by keeping the size of the division zone maximal for a longer period. In order to examine if the two chimeric genes synergistically influence each other and if the combination of both chimeric genes still increases leaf length, a cross was made between the two transgenic lines.

Figure 11A:
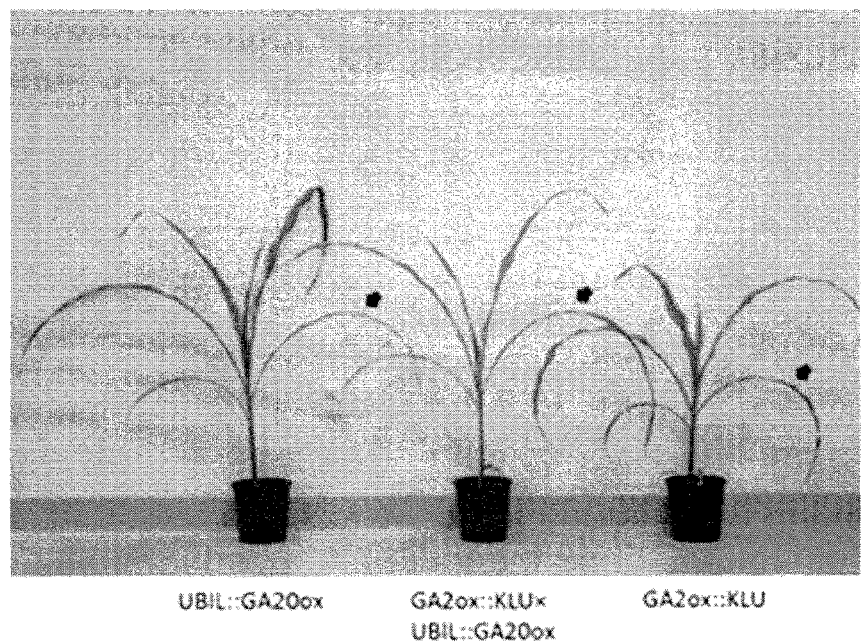
FIGS. 11A-11C: Phenotypes of the cross GA2OX::KLUH×UBIL::GA20Ox and its respective parents.
Figure 11B:
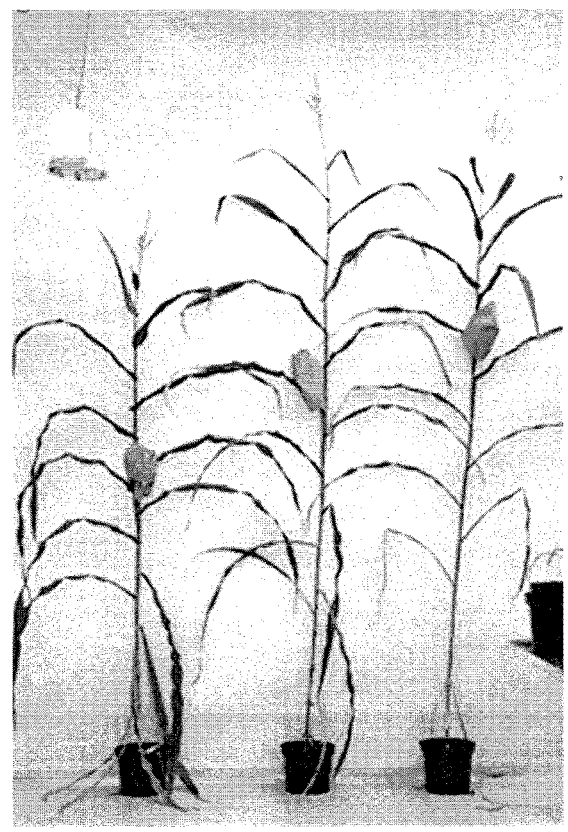
Figure 11C:
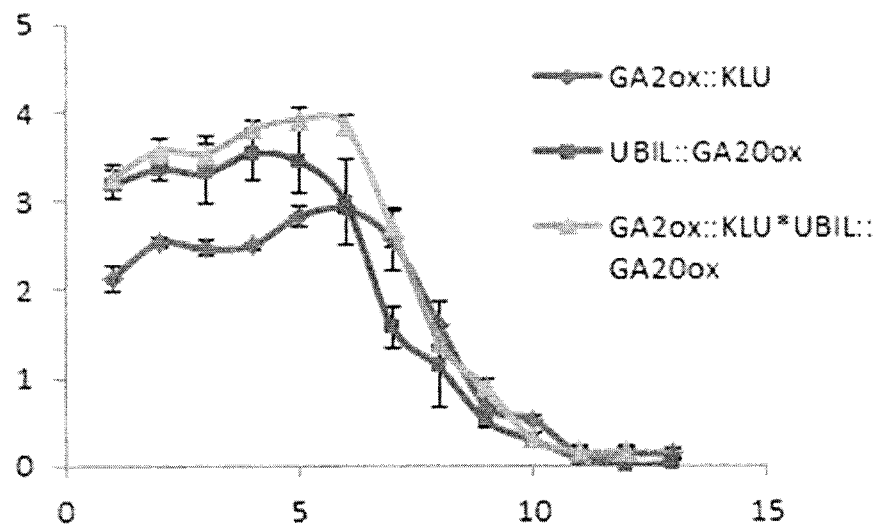

The LER of leaf 4 of the resulting GA2ox::KLUH× UBIL::GA20ox cross showed equally high growth rate as UBIL::GA20ox; and at day 7 of the growth of leaf 4, the cross showed the same growth rate as GA2ox::KLUH, when the growth rate of UBIL::GA20ox already decreased to a lower level. This chimeric gene combination in the hybrid leads to the additive increase of final leaf length and leaf area. In addition, the final leaf length and leaf area of leaf 2 was measured, which is similar to what was seen in leaf 4. No significant heterosis was observed in GA2ox::KLUH× UBIL::GA20ox mature plants phenotype, although the combination showed highest plant height and plant weight (see FIG. 11B; Table 5). In conclusion, it was shown that the chimeric gene combination (GA2ox::KLUH×UBIL::GA20ox) took the improved phenotype from each parent plant, e.g., the height of UBIL::GA2ox and the bigger leaf area from GA2ox::KLUH.

TABLE 5

Plant parameters of the cross GA2OX::KLUH x UBIL::GA20Ox and its respective parents

|  | WT | GA2ox::KLUH | UBIL::GA20ox | GA2ox::KLUHx UBIL::GA20ox |
|---|---|---|---|---|
| leaf 2 area | 11.01 * | 15.75 * | 14.09 * | 20.11 |
| leaf 4 length | 551.3 * | 636 * | 733.7 | 840 |
| leaf 4 area | 73.4 * | 93.28 * | 87.93 * | 129.76 |
| Plant height | 218.3 * | 23.6 * | 283.9 | 341.6 |
| plant weight | 530 | 537.3 | 438.2 | 552.6 |
| root length | 12.3 | 7.07 | 40.1 * | 10.3 |
| crown root No. | 2.3 | 2 | 3.25 * | 2.3 |
| flower length | 25.3 * | 26.6 | 33.5 | 34.35 |
| tassel branches | 10 * | 12 | 13.6 | 13 |

Asterisks indicate significant differences compared to GA2ox::KLUHxUBIL::GA20ox with p < 0.05.

Figure 12:
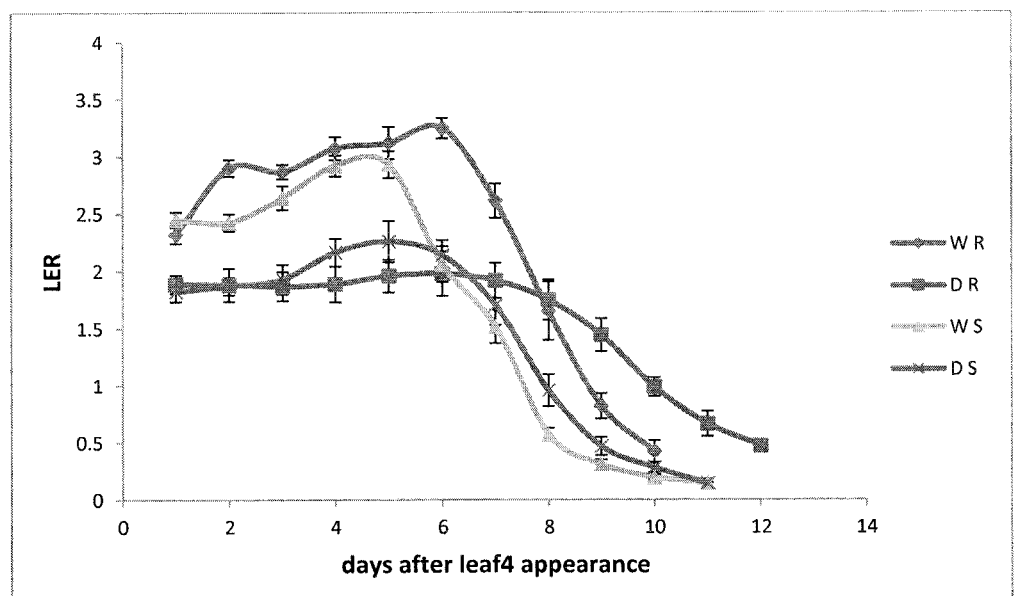
FIG. 12: Growth of the transgenic corn plants harboring the chimeric gene GA2ox::KLUH under mild drought stress. W indicates plants under well-watered condition; D indicates plants under mild drought stress; R and S refer to resistant and sensitive plants.

6. Growth of the Transgenic Corn Plants Harboring the Chimeric Gene GA2ox::KLUH Under Stress Conditions When transgenic corn plants harboring the chimeric gene GA2ox::KLUH was subjected to mild drought stress, no significant difference was observed in final leaf length (P_value=0.95), but a bigger reduction of LER (P_value=0.035) and a longer growth period (P_value=0) have been found in resistant plants under mild drought (see FIG. 12).

7. Non-Limiting Examples of Suitable GA2 Oxidase Promoters (Derived from Zea mays) that can be Used to Construct Chimeric Genes of the Disclosure SEQ ID NO:4: ZmGA2ox1 promoter (GRMZM2G127757; 2489 bp); this promoter is active in the growing leaf SEQ ID NO:5: ZmGA2ox2.1 promoter (GRMZM2G078798_T01; GRMZM2G078798_T02; GRMZM2G078798_T04; 2505 bp); Three transcript patterns GRMZM2G078798_T01; GRMZM2G078798_T02; GRMZM2G078798_T04 start at the same position. Thus, same promoter can be used. This promoter is active in growing leaves.

SEQ ID NO:6: ZmGA2ox2.1 promoter (GRMZM2G078798_T03; 2404 bp); GRMZM2G078798_T03 starts later in genome than the previous three transcripts (three transcript patterns GRMZM2G0787981_01; GRMZM2G078798_T02; GRMZM2G078798_T04). This promoter is active in growing leaves.

SEQ ID NO:7: ZmGA2ox2.2 promoter (GRMZM2G176963_T01; 2500 bp). This promoter is active in the cob of corn.

SEQ ID NO:8: ZmGA2ox3.1 promoter (GRMZM2G022679_T01; 2494 bp). This promoter is active in growing leaves.

SEQ ID NO:9: ZmGA2ox3.2 promoter (GRMZM2G031724; 2046 bp). This promoter is active in growing leaves and was used in Example 1.

SEQ ID NO:10: ZmGA2ox4 promoter (GRMZM2G427618_T01; 2120 bp). This promoter is active in growing leaves.

SEQ ID NO:11: ZmGA2ox6.2 promoter (GRMZM2G153359_T01; 2467 bp). This promoter is active in growing leaves.

SEQ ID NO:12: ZmGA2ox7.1 promoter (GRMZM2G051619_T01; 2456 bp). This promoter is active in growing leaves and in embryo.

SEQ ID NO:13: ZmGA2ox7.2 promoter (GRMZM2G152354_T01; 2500 bp). This promoter is active in the cob.

SEQ ID NO:14: ZmGA2ox7.3 promoter (GRMZM2G031432_T01; 2472 bp). This promoter is active in leaves and in the SAM.

8. Non-Limiting Examples of KLUH Orthologous Genes that can be Used to Construct Chimeric Genes of the Disclosure SEQ ID NO:15: >CYP78A5 (AtKLUH) AT1G13710
SEQ ID NO:16: >CYP78A1 (ZmKLUH) GRMZM2G167986
SEQ ID NO:17: >ZmKLUH-LIKE-GRMZM2G054603
SEQ ID NO:18: >CYP78A11 (OsPLA1) Os10g0403000
SEQ ID NO:19: >CYP78A7-AT5G09970
SEQ ID NO:20: >CYP78A27 (PpKLUH1) PP00504G00010.1
SEQ ID NO:21: >CYP78A28 (PpKLUH2) PP00134G00010.1

REFERENCES

Anastasiou E., S. Kenz, M. Gerstung, D. MacLean, J. Timmer, C. Fleck and M. Lenhard (2007). Control of Plant Organ Size by KLUH/CYP78A5-Dependent Intercellular Signaling. *Developmental Cell* 13:843-856.

Coussens G., S. Aesaert, W. Verelst, M. Demeulenaere, S. De Buck, E. Njuguna, D. Inze, and M. Van Lijsebettens (2012). Brachypodium distachyon promoters as efficient building blocks for transgenic research in maize. *Journal of Experimental Botany* 63:4263-4273.

De Block M., A. Sonville and D. Debrouwer (1995). The selection mechanism of phosphinothricin is influenced by the metabolic status of the tissue. *Planta* 197:619-626.

Karimi M., D. Inzé, M. Van Lijsebettens, and P. Hilson (2013). Gateway vectors for transformation of cereals. *Trends in Plant Science* 18:1-4.

Kazama T., Y. Ichihashi, S. Murata, and H. Tsukaya (2010). The Mechanism of Cell Cycle Arrest Front Progression Explained by a KLUH/CYP78A5-dependent Mobile Growth Factor in Developing Leaves of *Arabidopsis thaliana*. *Plant and Cell Physiology* 51:1046-1054.

Nelissen H., B. Rymen, F. Coppens, S. Dhondt, F. Fiorani, and G. S. Beemster (2013). "Kinematic Analysis of Cell Division in Leaves of Mono- and Dicotyledonous Species: A Basis for Understanding Growth and Developing Refined Molecular Sampling Strategies." In *Plant Organogenesis*, I. De Smet, ed. (Humana Press), pp. 247-264.

Nelissen H., B. Rymen, Y. Jikumaru, K. Demuynck, M. Van Lijsebettens, Y. Kamiya, D. Inze, and Gerrit T. S. Beemster (2012). "A Local Maximum in Gibberellin Levels Regulates Maize Leaf Growth by Spatial Control of Cell Division." *Current Biology* 22:1183-1187.

The invention claimed is:

1. A method for producing a plant cell, wherein the method comprises:
   identifying a promoter region of a plant GA2 oxidase gene that is active in the growth zone of a plant leaf,
   identifying a DNA region encoding a plant CYP78A5 protein;
   operatively linking the identified promoter to the identified DNA region encoding a plant CYP78A5 protein and a 3' end region comprising transcription termination and polyadenylation signals functioning in cells of a plant to form a chimeric gene;
   introducing into or transforming a plant cell with the chimeric gene,
   selecting a plant cell with a stable expression of the chimeric gene and
   determining that a plant generated from the selected plant cell has an increased yield as compared to a corresponding wildtype plant.

2. The method according to claim 1, wherein the plant cell is a plant cell of a crop plant.

3. The method according to claim 2, wherein the plant cell is a plant cell of a cereal plant.

4. The method according to claim 2, wherein the plant cell is a plant cell of a grass.

5. The method according to claim 1, further comprising, generating a seed or a plant tissue comprising the plant cell.

* * * * *